United States Patent
Robert et al.

(10) Patent No.: US 9,575,147 B2
(45) Date of Patent: Feb. 21, 2017

(54) NUCLEAR QUADRUPOLE RESONANCE SYSTEM AND METHOD OF USING THE SAME TO REMOVE INTERFERENCE COMPONENTS FROM SENSOR SIGNALS

(71) Applicant: MORPHO DETECTION, INC., Newark, CA (US)

(72) Inventors: Hector Robert, San Diego, CA (US); Erik Edmund Magnuson, Cardiff, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 725 days.

(21) Appl. No.: 13/974,629

(22) Filed: Aug. 23, 2013

(65) Prior Publication Data

US 2014/0070810 A1    Mar. 13, 2014

Related U.S. Application Data

(60) Provisional application No. 61/698,243, filed on Sep. 7, 2012, provisional application No. 61/800,923, filed on Mar. 15, 2013.

(51) Int. Cl.
    *G01R 33/36*     (2006.01)
    *G01N 24/08*     (2006.01)
    (Continued)

(52) U.S. Cl.
    CPC ........... *G01R 33/3628* (2013.01); *G01R 33/36* (2013.01); *G01R 33/441* (2013.01); *G01N 24/084* (2013.01);
    (Continued)

(58) Field of Classification Search
    CPC ... G01R 33/36; G01R 33/3628; G01R 33/441; G01R 33/3415; G01R 33/3664; G01N 24/084
    See application file for complete search history.

(56) References Cited

U.S. PATENT DOCUMENTS

| 4,825,162 A | 4/1989 | Roemer et al. |
| 6,054,856 A * | 4/2000 | Garroway ............ G01R 33/343 324/309 |

(Continued)

FOREIGN PATENT DOCUMENTS

| JP | 0735871 A | 2/1995 |
| WO | 2004068159 A1 | 8/2004 |

OTHER PUBLICATIONS

Combined Search and Examination Report from UKIPO, dated Jan. 31, 2014, for co-pending GB patent application No. GB1315776.3 (8 pgs).

(Continued)

*Primary Examiner* — G. M. Hyder
(74) *Attorney, Agent, or Firm* — Armstrong Teasdale LLP

(57) ABSTRACT

A nuclear quadrupole resonance (NQR) sensor assembly includes an active sensor coil configured to transmit radiofrequency (RF) signals to an object of interest and receive return RF signals from the object of interest to generate sensor signals substantially representative of the return signals. The at least one reference coil is configured to receive environmental RF signals to generate reference signals at least partially representative of the environmental RF signals. The at least one reference coil is co-located with the active sensor coil. The active sensor coil and the at least one reference coil are in communication with a correction unit configured to remove interference components from the sensor signals using the reference signals.

20 Claims, 14 Drawing Sheets

(51) Int. Cl.
 *G01R 33/44* (2006.01)
 *G01R 33/3415* (2006.01)
(52) U.S. Cl.
 CPC ....... *G01R 33/3415* (2013.01); *G01R 33/3664* (2013.01)

(56) References Cited

U.S. PATENT DOCUMENTS

| | | |
|---|---|---|
| 6,486,838 B1 | 11/2002 | Smith et al. |
| 6,924,644 B2 | 8/2005 | Suits et al. |
| 7,292,033 B2 | 11/2007 | Pusiol |
| 7,714,791 B2 | 5/2010 | Lavedas |
| 7,791,342 B2 | 9/2010 | Sauer et al. |
| RE43,264 E | 3/2012 | Walsh |
| 2005/0146331 A1 | 7/2005 | Flexman et al. |
| 2006/0113998 A1* | 6/2006 | Itozaki ............... G01V 3/14 324/326 |
| 2011/0210728 A1 | 9/2011 | Somasundaram et al. |

OTHER PUBLICATIONS

Long, et al., Methods for Reducing RF Interference for Improved NQR Detection of Landmines, 2003, pp. 108-118, vol. 5089, Detection and Remediation Technologies for Mines and Miinelike Targets VIII, http://proceedings.spiedigitallibrary.org/ on Sep. 1, 2012 Terms of Use: http://spiedl.org/terms.

Liu, et al., Radio Frequency Interference Suppression for the Quadrupole Resonance Confirming Sensor, 2004, pp. 834-842, vol. 5415, Detection and Remediation Technologies for Mines and Miinelike Targets IX, http://proceedings.spiedigitallibrary.org/ on Sep. 1, 2012 Terms of Use: http://spiedl.org/terms.

* cited by examiner

NUCLEAR QUADRUPOLE RESONANCE SYSTEM AND METHOD OF USING THE SAME TO REMOVE INTERFERENCE COMPONENTS FROM SENSOR SIGNALS

CROSS REFERENCE TO RELATED APPLICATIONS

This application claims the priority of Provisional Patent Application Ser. No. 61/698,243, entitled "NUCLEAR QUADRUPOLE RESONANCE SYSTEM AND METHOD OF USING THE SAME", which was filed on Sep. 7, 2012, and Provisional Patent Application Ser. No. 61/800,923, entitled "NUCLEAR QUADRUPOLE RESONANCE SYSTEM AND METHOD OF USING THE SAME", which was filed on Mar. 15, 2013, and both of which are hereby incorporated by reference in their entirety.

BACKGROUND OF THE INVENTION

The embodiments described herein relate generally to a nuclear quadrupole resonance (NQR) detection system and, more particularly, to an NQR detection system for reducing environmental radiofrequency interference signals in a detection signal generated by the NQR system.

NQR is a radiofrequency (RF) spectroscopic technique that may be used to detect a presence of materials containing quadrupolar nuclei, such as nitrogen-14, potassium-39, chlorine-35, and chlorine-37, that may indicate a material of interest is present. As used herein, the term "material of interest" refers to explosives, narcotics, home-made explosives (HME), and/or any other material that may compose a threat in an inspected region. NQR has been used for baggage and parcel screening, narcotics detection and/or explosives detection, such as detection of buried Improvised Explosives Devices (IED), personnel screening, and/or landmine detection.

At least some known NQR systems include an RF transmission device that transmits waves in the RF portion of the energy spectrum at the NQR frequencies associated with the materials of interest. NQR arises from the electrical interaction between the electric quadrupole moment of the NQR-active nuclei and the electric field gradient at the position of these nuclei created by the electrical charge distributions in the molecules of the material of interest. The transmitted RF waves excite transitions between energy levels defined by the electrical interactions. When the nuclei transition back to the equilibrium state, an NQR response is received from the nuclei. Such known NQR systems also include a receiving device that receives the NQR responses with the resonant frequencies. A material to be scanned is positioned in or near a tuned, resonant inductive element (usually referred to as a "coil") that detects NQR signals induced by pulsed RF excitation fields.

In some applications of NQR, a sensor, such as an NQR coil, operates unshielded or partially shielded from electromagnetic (EM) fields. However, such a sensor may suffer from low signal-to-noise ratios (SNR), which may be further aggravated by a presence of external or background radio frequency interferences (RFI). The RFI may be caused by far away sources (i.e., radio stations) and/or from the presence of other equipment in the vicinity of the sensor (i.e., electronic and electrical equipment). In order to operate with low false alarm rate (FAR) levels when the sensor is deployed outside shielded enclosures, it is desirable that the NQR sensor be insensitive or immune to the presence of external RFI and/or environmental RF noise.

At least one known sensor design for improving rejection of environmental interferences includes gradiometer coils. The gradiometer coils are immune to EM fields that are uniform in space. As such, the gradiometer coils are sensitive only to a spatial derivative of the EM fields. In addition, such environmental interference may also include significant gradients that have magnitudes large enough to not be fully canceled by the gradiometer coils.

Another known sensor is a gradiometer that includes two separate coils wound in opposite directions and connected in series. Alternatively, the two coils are wound in the same direction but a phase inversion is performed in one of the coils before the signals are combined at a receiver. Noise that is detected by the two coils arrives at the receiver as two signals with opposite phases, leading to self-cancellation of the noise. A sample is always placed closer to one coil than to the other coil such that a NQR signal of the sample is not cancelled. However, this sensor has the disadvantage of reducing the SNR because the second coil adds thermal noise to the NQR signal upon summation of the signals.

Further, known research has proposed the use of excitation RF pulse sequences with composite pulses for cancellation of spurious signals. However, the use of such excitation RF pulse sequences results in significant signal-to-noise degradation that adversely impacts the detection performance of an NQR sensor implementing the excitation RF pulse sequences.

At least one known portable NQR system (i.e. an NQR wand, a backpack mine detector, and/or a landmine detector) uses a set of ancillary antennas or coils, such as a three antennas, for active RFI cancellation. The ancillary antennas are independent of a transmitting/receiving NQR sensor, such as being positioned several feet away from the receiving NQR sensor. The ancillary antennas sample three perpendicular components of external EM radiation that may interfere with the operation of the receiving NQR sensor. The ancillary antennas may be referred to as "RFI antennas" and are separated from the receiving NQR sensor (the "main NQR sensor") and are located at a sufficient distance from the main NQR coil to avoid interferences between the RFI antennas and the main NQR coil. Such an NQR system provides relatively good performance in RFI cancellation but does not achieve the RFI rejection desired when the interferences do not correlate, for example, when the source of RFI is closer to the main NQR coil and/or when there are multiple paths/sources of RFI.

Phased-coil arrays are known for use in Magnetic Resonance Imaging (MRI) to improve spatial resolution and/or SNRs. In phased-coil arrays, nuclear magnetic resonance (NMR) responses from different surface coils within the array are combined to produce a single composite NMR image of the total sample. In at least one known phased-coil array, problematic interactions among nearby surface coils of the array are substantially reduced by overlapping adjacent coils to provide zero mutual inductance between adjacent coils and by attaching low-input-impedance pre-amplifiers to each of the coils, thus eliminating interference among next nearest and more distant neighbors. A phased array of coils allows simultaneous acquisition of multiple signals with minimal interference between them. However, each coil of the phased array receives NMR responses from a scanned object and any RFI near the scanned object because each coil of the array transmits and receives signals.

BRIEF DESCRIPTION OF THE INVENTION

In one aspect, a nuclear quadrupole resonance (NQR) sensor assembly is provided. The NQR sensor assembly includes an active sensor coil configured to transmit radiofrequency (RF) signals to an object of interest and receive return RF signals from the object of interest to generate sensor signals substantially representative of the return signals. The at least one reference coil is configured to receive environmental RF signals to generate reference signals at least partially representative of the environmental RF signals. The at least one reference coil is co-located with the active sensor coil. The active sensor coil and the at least one reference coil are in communication with a correction unit configured to remove interference components from the sensor signals using the reference signals.

In another aspect, a nuclear quadrupole resonance (NQR) detection system is provided. The NQR system includes an active sensor coil configured to transmit radiofrequency (RF) signals to an object of interest and receive return RF signals from the object of interest to generate sensor signals substantially representative of the return RF signals. The NQR system also includes at least one reference coil configured to receive environmental RF signals to generate reference signals at least partially representative of the environmental RF signals. The at least one reference coil is co-located with the active sensor coil. The NQR system further includes a correction unit in communication with the active sensor coil and the at least one reference coil. The correction unit is configured to remove interference components from the sensor signal using the at least one reference signal.

In yet another aspect, a method for performing nuclear quadrupole resonance (NQR) detection is provided. The method includes generating sensor signals from an active sensor coil and reference signals from at least one reference coil. The at least one reference coil is co-located with the active sensor coil. The method also includes reducing an interference component of the sensor signals using the reference signals to generate corrected signals. The method further includes determining a presence of a target material based on the corrected signals.

BRIEF DESCRIPTION OF THE DRAWINGS

FIG. 1 is a schematic view of an exemplary detection system;

FIG. 2 is a schematic view of an exemplary sensor assembly for use with the detection system shown in FIG. 1;

FIG. 3 is a schematic side view of a portion of the detection system shown in FIG. 1;

FIG. 4 is a three-dimensional (3D) graphical representation of magnetic field strengths of a first coil that may be used with the sensor assembly shown in FIGS. 2 and 3;

FIG. 5 is a graphical representation of nuclear quadrupole resonance (NQR) intensities of the first coil shown in FIG. 4 that may be used with the sensor assembly shown in FIGS. 2 and 3;

FIG. 6 is a 3D graphical representation of magnetic field strengths of a second coil that may be used with the sensor assembly shown in FIGS. 2 and 3;

FIG. 7 is a graphical representation of NQR intensities of the second coil shown in FIG. 6 that may be used with the sensor assembly shown in FIGS. 2 and 3;

FIG. 8 is a flowchart of a method for using the detection system shown in FIGS. 1-3;

FIG. 9 is a schematic view of an exemplary correction unit for use with the detection system shown in FIG. 1;

FIG. 10 is a schematic view of an alternative exemplary correction unit for use with the detection system shown in FIG. 1;

FIG. 11 is a schematic view of a first alternative exemplary detection system;

FIG. 12 is a schematic view of an exemplary sensor assembly for use with the detection system shown in FIG. 11;

FIG. 13 is a schematic view of a first alternative exemplary sensor assembly for use with the detection system shown in FIGS. 1-3 and/or the detection system shown in FIG. 11;

FIG. 14 is a schematic view of a second alternative exemplary sensor assembly for use with the detection system shown in FIGS. 1-3 and/or the detection system shown in FIG. 11;

FIG. 15 is a schematic view of a third alternative exemplary sensor assembly for use with the detection system shown in FIGS. 1-3 and/or the detection system shown in FIG. 11; and FIG. 16 is a schematic view of a fourth alternative exemplary sensor assembly for use with the detection system shown in FIGS. 1-3 and/or the detection system shown in FIG. 11.

DETAILED DESCRIPTION OF THE INVENTION

The embodiments described herein provide an unshielded or partially unshielded nuclear quadrupole resonance (NQR) detection system and a method for reducing or eliminating effects of external and/or background radio frequency interferences (RFI) in the NQR detection system. More specifically, the embodiments described herein include an NQR sensor assembly having multiple coils, such as surface coils, arranged for simultaneously receiving radiofrequency (RF) signals. The received RF signals are combined to separate NQR signals received from a scanned object from background RFI that may adversely impact NQR detection in unshielded or partially unshielded NQR sensors.

In one embodiment, a set of two or more decoupled RF coils/antenna in a phased coil array are used for active cancellation of external or background RFI in the NQR detection system. This exemplary embodiment uses a set of independent, co-located coils for simultaneous acquisition of NQR signals from a target sample and external EM interferences and/or RFI near or surrounding the target sample. This embodiment further includes data processing algorithms for coherent mitigation of the EM interferences and/or RFI. More specifically, the embodiments described herein take advantage of a reception pattern of a localized coil in order to extract additional information from the NQR signals from the target sample and from the external RFI.

An exemplary NQR detection described herein includes a simple linear array of two coils and/or antennas that is applicable to, for example, a handheld nuclear quadrupole resonance (NQR) system. A first coil of the array is an active transmit/receive (TX/RX) NQR sensor coil to target a scan area, and a second coil of the array is geometrically decoupled from the first coil and serves only as a receive antenna (RX1) for sampling external RFI. Additional circuitry may be included to practically eliminate coupling (i.e., mutual inductance) between the two coils. Subtraction of interference from the NQR signals acquired by the first coil may be accomplished using adaptive mitigation algorithms and/or estimation/subtraction algorithms based on the RFI signals acquired by the second coil.

An alternative exemplary NQR detection system described herein includes a phased-coil array having three decoupled coils. A first coil is the active transmit/receive (TX/RX) NQR sensor coil and the two other coils (RX1 and RX2) receive the external RFI. Interference cancellation from the NQR signals obtained by the first coil is achieved using adaptive mitigation or by estimation/subtraction algorithms based on the RFI signals acquired by the other two coils. Although two and three coil arrays are described herein, it should be understood that the phased-coil array may include any suitable number of coils. Further, different coil geometries, such as rectangular, square, or circular, may be used in the phased-coil arrays described herein.

Figure 1:
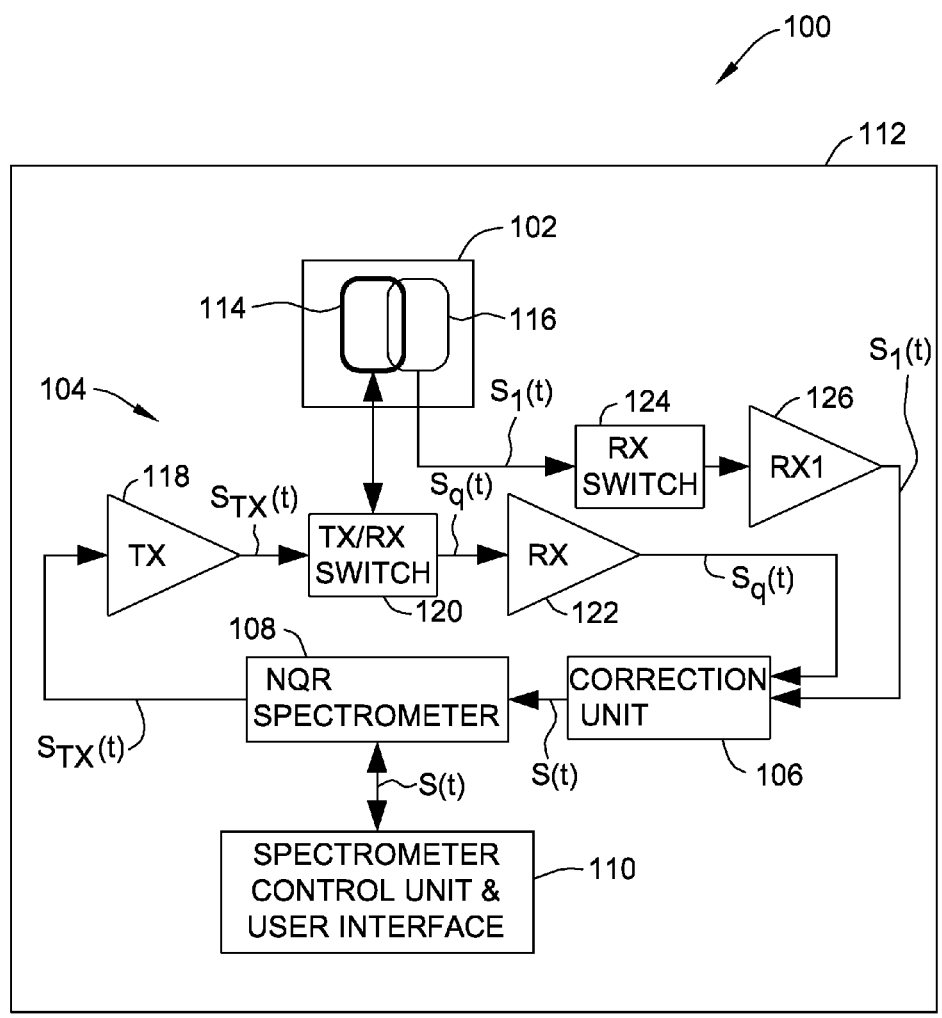
FIGS. 1-16 show exemplary embodiments of the systems and methods described herein.
Figure 2:
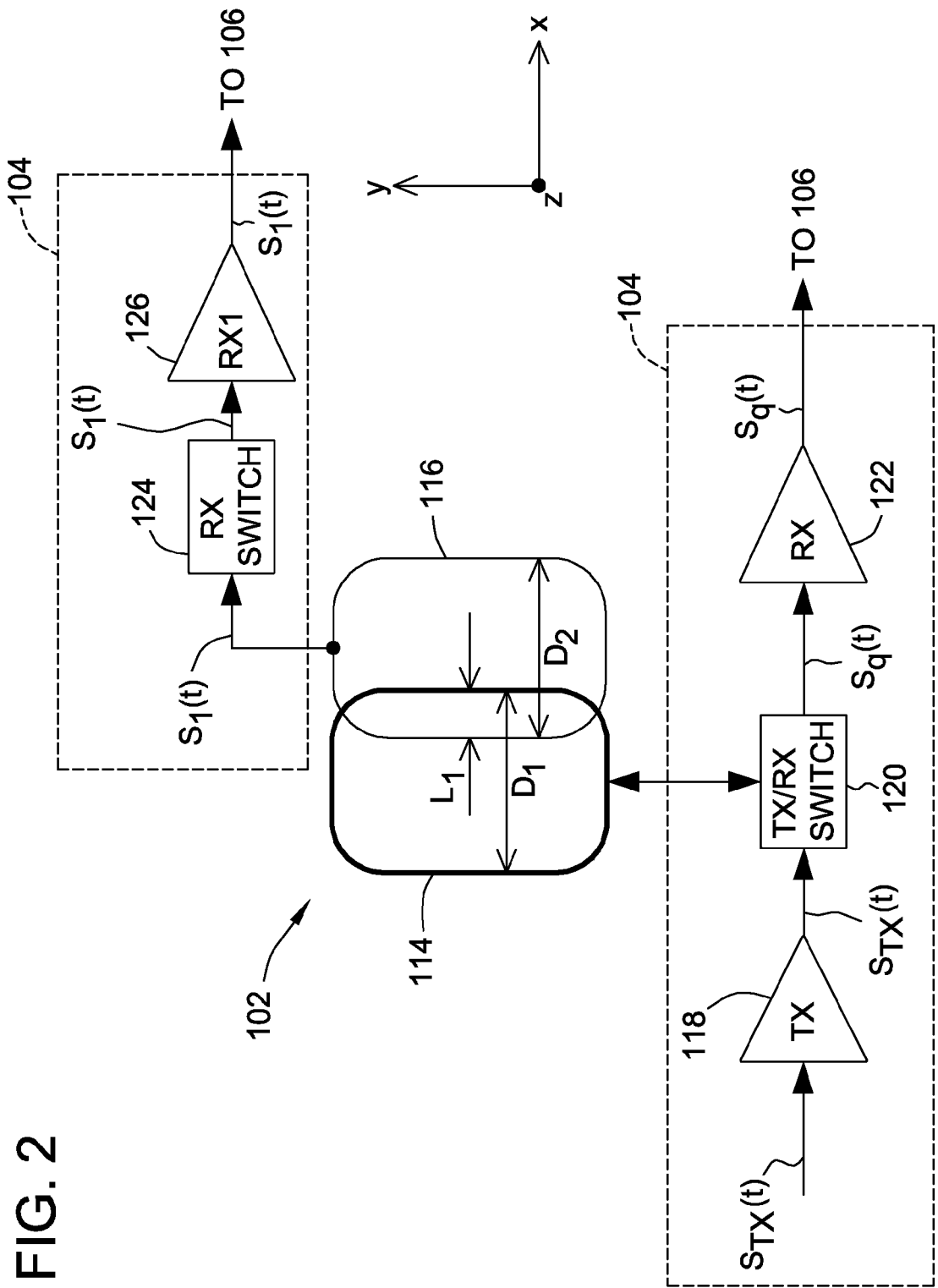
Figure 3:
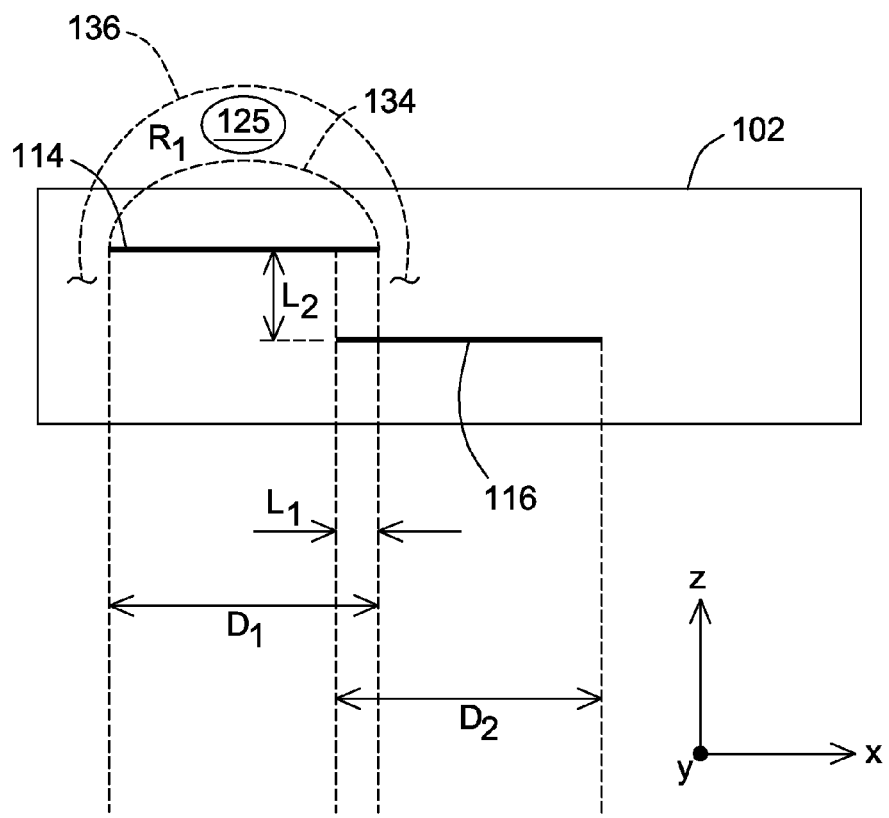

FIG. 1 is a schematic view of an exemplary detection system 100 configured to perform nuclear quadrupole resonance (NQR) scanning FIG. 2 is a schematic view of an exemplary sensor assembly 102 for use with detection system 100. FIG. 3 is a schematic side view of a portion of detection system 100. Detection system 100 may be a man-portable device, such as a wand and/or a landmine detector. Detection system 100 is unshielded or partially shielded and may be combined with any other suitable detectors. When detection system 100 is combined with another detector, the other detector may be the primary detector for locating a target object or target sample, and detection system 100 may be used to determine if a target material, compound, and/or element is present in the target object and/or target sample.

Detection system 100 includes sensor assembly 102, control circuitry 104, a cancellation or correction unit 106, a spectrometer 108, and a control unit 110 within a housing 112. Although correction unit 106 is shown as being separate from spectrometer 108, correction unit 106 may be included in spectrometer 108 and/or control unit 110. Further, correction unit 106 may be hardware or software embodied on hardware within detection system 100. Sensor assembly 102 is an NQR sensor that includes at least two coils 114 and 116 (both described in more detail below). Control circuitry 104 includes a transmit (TX) amplifier 118, a transmit/receive (TX/RX) switch 120, and a receive (RX) amplifier 122 in series between spectrometer 108 and correction unit 106 with TX/RX switch 120 coupled to first antenna or coil 114 of sensor assembly 102. Control circuitry 104 further includes a first receive (RX) switch 124 and a first reference receive (RX1) amplifier 126 coupled in series between second antenna or coil 116 and correction unit 106. Any amplifiers described herein may be low-impedance preamplifiers and/or any other suitable type of amplifier. Correction unit 106 is coupled in communication with spectrometer 108 and/or control unit 110, and control unit 110 and spectrometer 108 are coupled in communication with each other.

Referring to FIGS. 2 and 3, sensor assembly 102 extends in three dimensions, i.e., length-wise along an x-axis, height-wise along a y-axis, and depth-wise along a z-axis. The x-axis, y-axis, and z-axis are orthogonal to each other. Sensor assembly 102 includes first coil 114 as an NQR active sensor coil and second coil 116 as a reference coil. Sensor assembly 102 may include more than one reference coil (discussed further below). First coil 114 has a first loop diameter, or distance, $D_1$ and second coil 116 has a second loop diameter, or distance, $D_2$. In the exemplary embodiment, values for $D_1$ and $D_2$ are substantially similar. Alternatively, first coil 114 and second coil 116 may have any values for $D_1$ and $D_2$, respectively, that enable operation of sensor assembly 102 as described herein.

Also, in the exemplary embodiment, sensor assembly 102 is a phased-coil array configured to eliminate mutual inductance between coils 114 and 116. More specifically, first coil 114 overlaps second coil 116 by a length $L_1$ along the x-axis that substantially reduces mutual inductance between coils 114 and 116. Length $L_1$ has a value that is approximately 90% of the radius of first coil 114 and second coil 116, i.e., $0.9*D_{1\ or\ 2}/2$. Alternatively, $L_1$ has any value that enables operation of sensor assembly 102 as described herein. In addition, first coil 114 and second coil 116 are separated in the z-axis dimension by a length $L_2$ that has a very small value that enables operation of sensor assembly 102 as described herein (length $L_2$ shown larger than actual for clarity in FIG. 3). Therefore, first coil 114 and second coil 116 are positioned with respect to each other such that an overlap of in-phase and out-phase inductance facilitates cancelling mutual inductance. Coils 114 and 116 are tuned at the NQR resonance frequency of the sample of interest.

Figure 4:
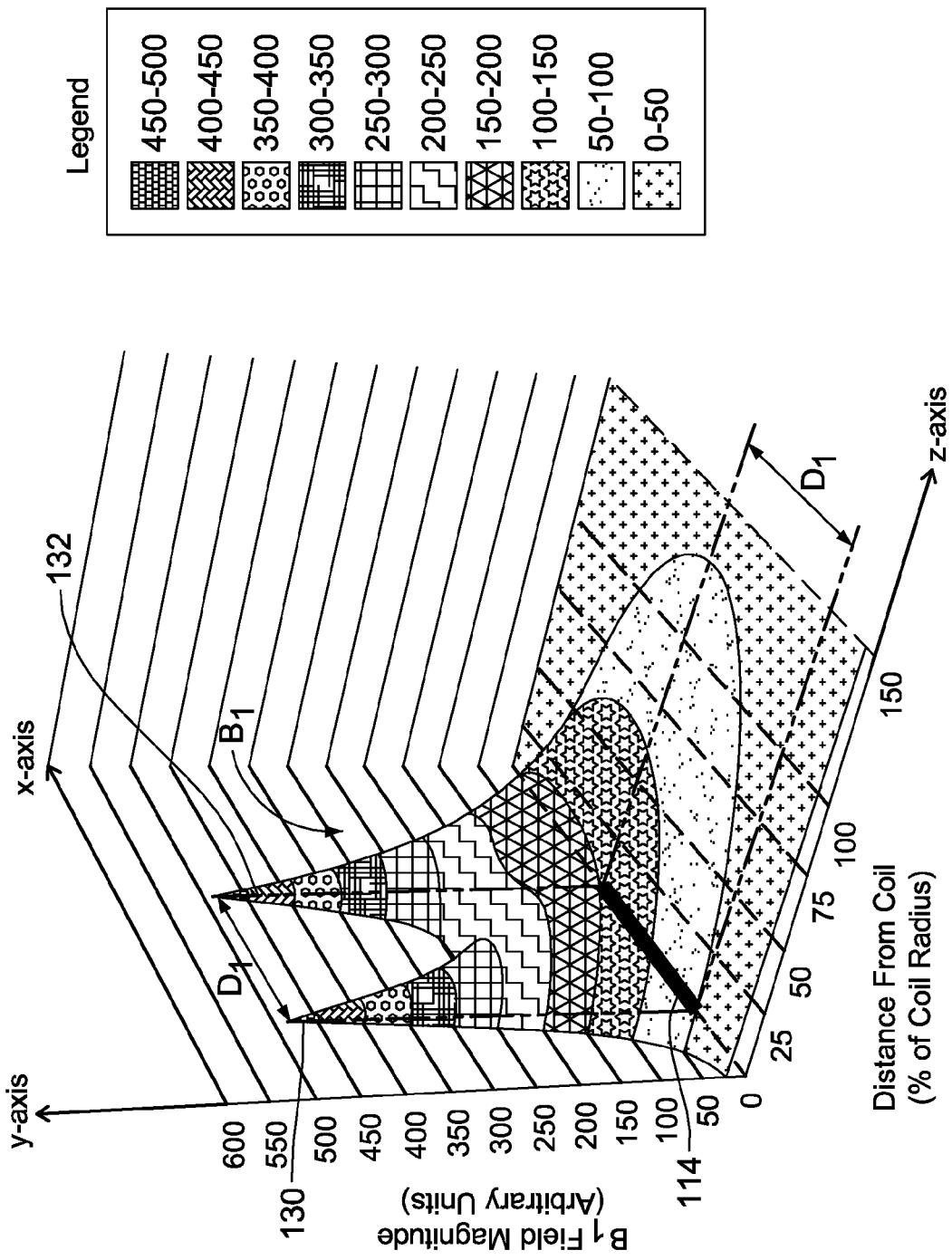

FIG. 4 is a three-dimensional (3D) graphical representation of magnetic field strengths of first coil 114 that may be used with sensor assembly 102 (shown in FIGS. 2 and 3). First coil 114 generates a magnetic field $B_1$. The y-axis represents scaler, i.e., numerical values of the strength of magnetic field $B_1$ in arbitrary units extending from 0 to 600 in increments of 50, as opposed to the height-wise dimension shown in FIGS. 2 and 3. The length-wise x-axis and depth-wise z-axis in FIG. 4 are consistent with the x-axis and z-axis in FIGS. 2 and 3. The x-axis in FIG. 4 is unitless and loop distance $D_1$ is shown. Magnetic field $B_1$ includes two substantially similar peaks 130 and 132 that are separated by loop distance $D_1$. The z-axis in FIG. 4 represents the distance from first coil 114 in the depth-wise dimension in units of percentage of the radius of first coil 114, i.e., $D_1/2$. The x-axis and the z-axis are not scaled to each other.

Figure 5:
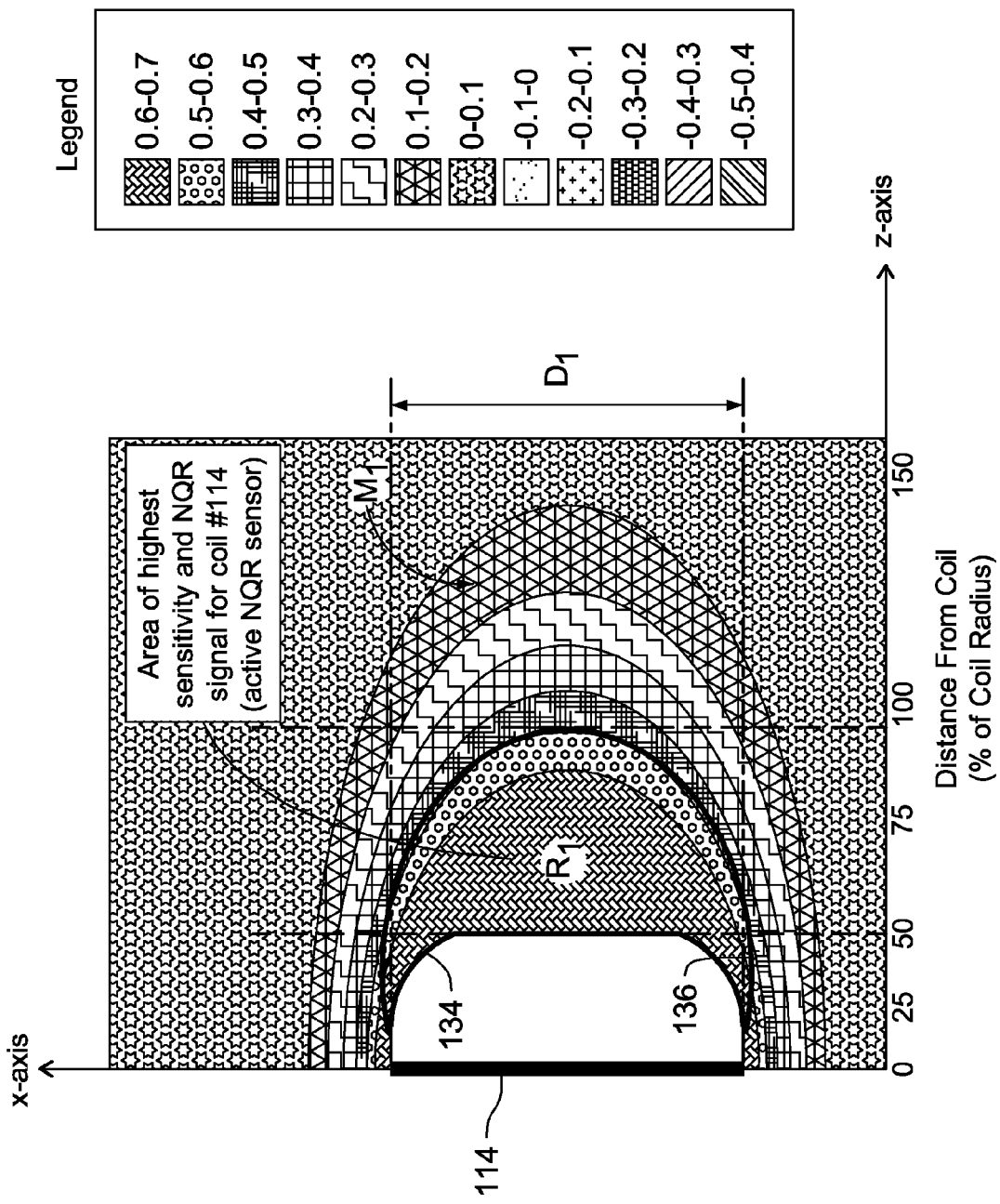

FIG. 5 is a graphical representation of nuclear quadrupole resonance (NQR) intensities, i.e., associated signal strength, of first coil 114 that may be used with sensor assembly 102 (shown in FIGS. 2 and 3). The orientations of length-wise x-axis and depth-wise z-axis in FIG. 5 are consistent with the x-axis and z-axis in FIGS. 2, 3, and 4. The x-axis in FIG. 5 is unitless and loop distance $D_1$ is shown. The z-axis in FIG. 5 represents the distance from first coil 114 in the depth-wise dimension in units of percentage of the radius of first coil 114, i.e., $D_1/2$. The x-axis and the z-axis are not scaled to each other. First coil 114 is configured to define an NQR sensitivity map $M_1$ that includes a region $R_1$ of highest sensitivity bounded by curves 134 and 136. The intensity values of the NQR signals are arbitrary and are normalized with respect to a predetermined maximum sensitivity, i.e., the greatest value of intensity is normalized to a value of 1.0. In the exemplary embodiment, curve 134 extends to approximately 50% of the value of the radius of first coil 114, i.e., 50% of $D_1/2$ along the z-axis. Similarly, curve 136 extends to approximately 90% of the value of the radius of first coil 114, i.e., 90% of $D_1/2$ along the z-axis.

Referring to FIGS. 2, 3, 4, and 5, when first coil 114 is in the transmit mode, pulsed signals STX(t) are transmitted from TX amplifier 118 to first coil 114 through TX/RX switch 120 to generate and transmit (RF) signals (not shown). When first coil 114 is in the receive mode, pulsed signals STX(t) are not transmitted to first coil 114. Rather, first coil 114 receives return RF signals (not shown) from target sample 125 in region $R_1$, where q indicates that the signal S is a sensor signal. As such, first coil 114 is configured as the NQR active sensor coil because first coil 114 is configured to transmit and receive RF signals.

Figure 6:
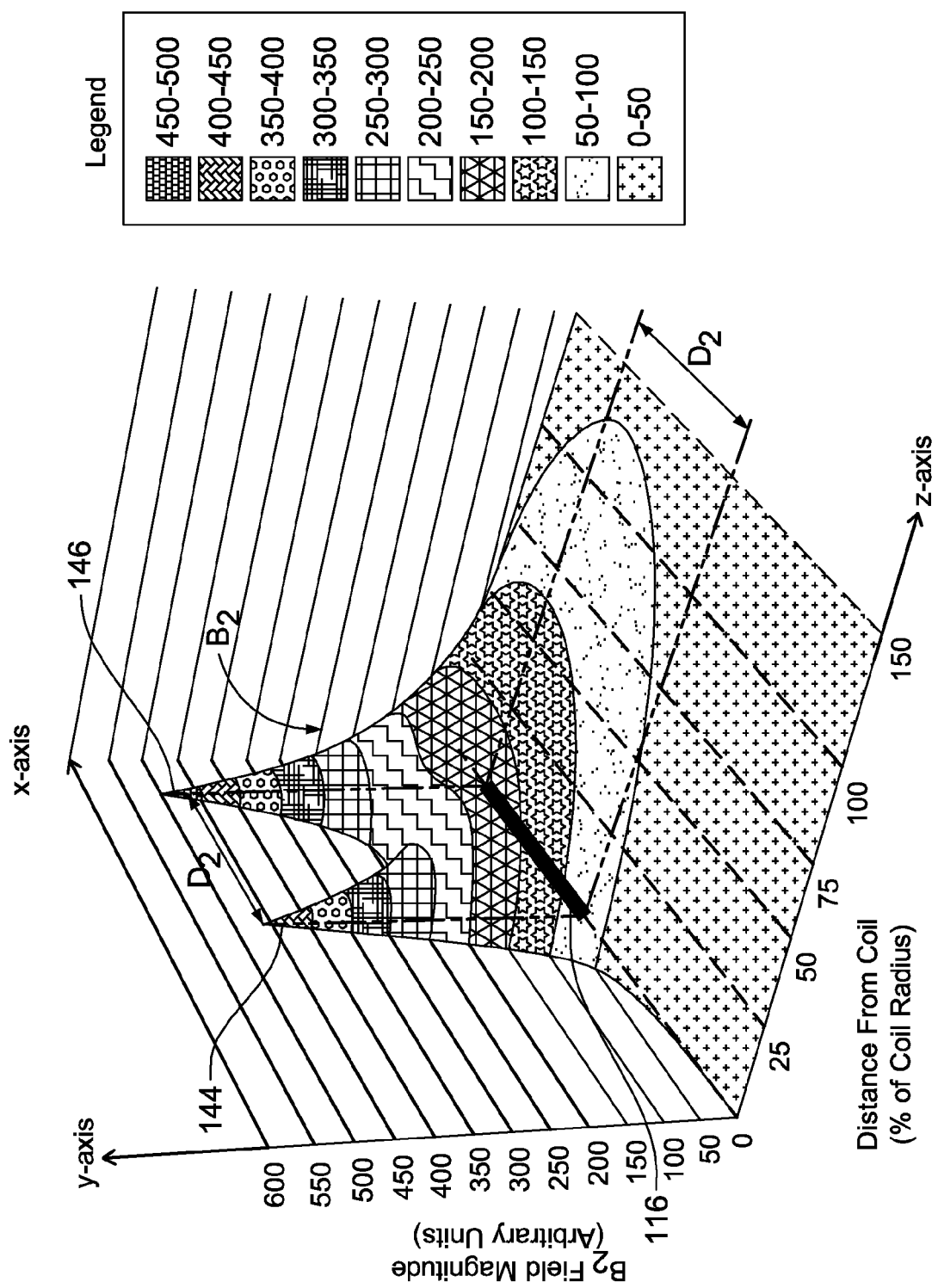

FIG. 6 is a 3D graphical representation of magnetic field strengths of second coil 116 that may be used with sensor assembly 102 (shown in FIGS. 2 and 3). Second coil 116 generates a magnetic field $B_2$. The y-axis represents scaler, i.e., numerical values of the strength of magnetic field $B_2$ in arbitrary units extending from 0 to 600 in increments of 50, as opposed to the height-wise dimension shown in FIGS. 2 and 3. The length-wise x-axis and depth-wise z-axis in FIG. 6 are consistent with the x-axis and z-axis in FIGS. 2, 3, 4, and 5. The x-axis in FIG. 6 is unitless and loop distance $D_2$ is shown. Magnetic field $B_2$ includes two substantially similar peaks 144 and 146 that are separated by loop distance $D_2$. The z-axis in FIG. 6 represents the distance from first coil 116 in the depth-wise dimension in units of percentage of the radius of second coil 116, i.e., $D_2/2$. The x-axis and the z-axis are not scaled to each other. Magnetic field $B_2$ is similar to magnetic field $B_1$ (shown in FIG. 4).

Figure 7:
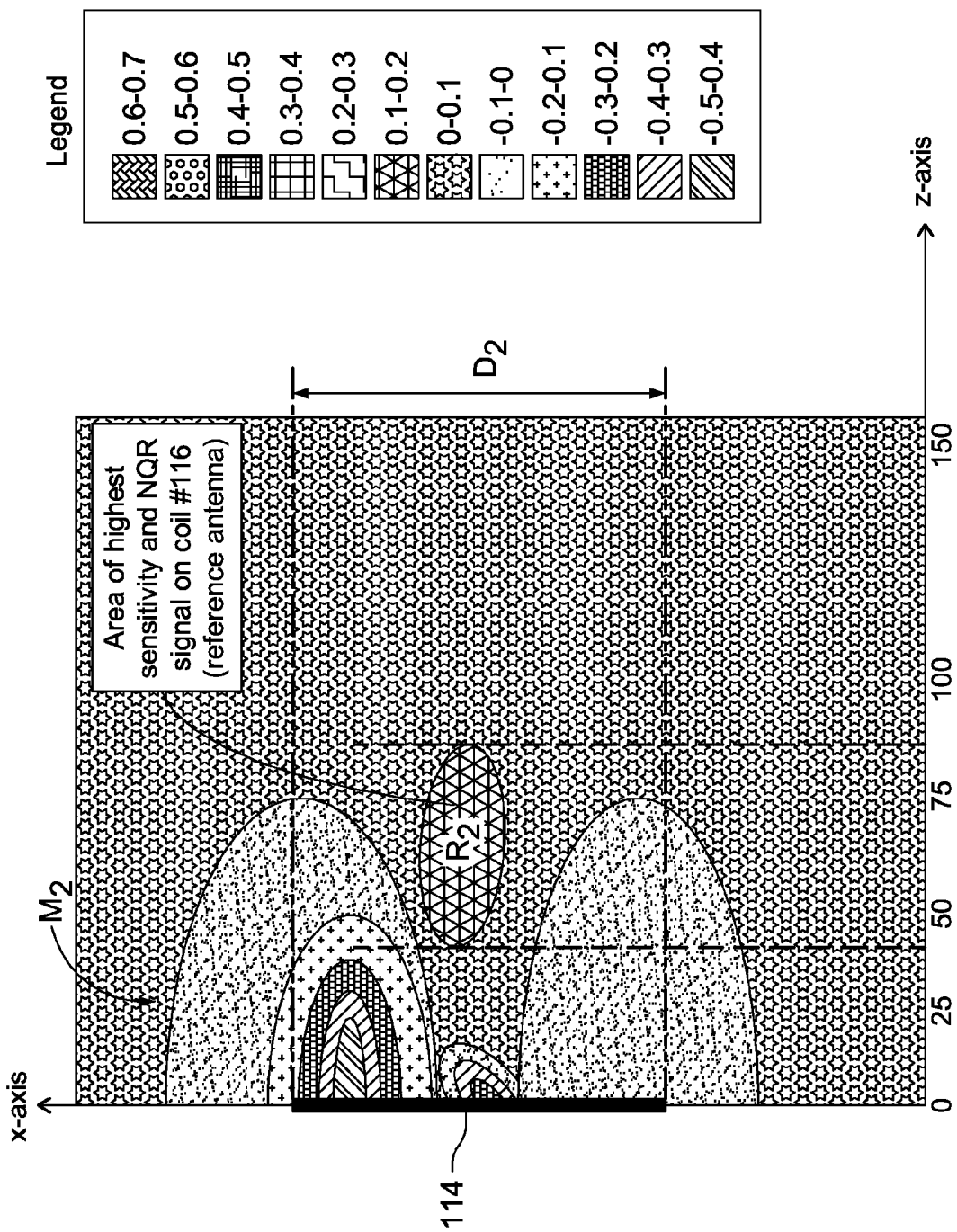

FIG. 7 is a graphical representation of nuclear quadrupole resonance (NQR) intensities, i.e., associated signal strength, of second coil 116 that may be used with sensor assembly 102 (shown in FIGS. 2 and 3). The orientations of length-wise x-axis and depth-wise z-axis in FIG. 7 are consistent with the x-axis and z-axis in FIGS. 2, 3, 4, 5, and 6. The x-axis in FIG. 7 is unitless and loop distance $D_2$ is shown. The z-axis in FIG. 7 represents the distance from second coil 116 in the depth-wise dimension in units of percentage of the radius of second coil 116, i.e., $D_2/2$. The x-axis and the z-axis are not scaled to each other. Second coil 116 is configured to define an NQR sensitivity map $M_2$ that includes a region $R_2$ of highest sensitivity. The intensity values of the NQR signals are arbitrary and are normalized with respect to a predetermined maximum sensitivity, i.e., the greatest value of intensity is normalized to a value of 1.0. The intensity values of region $R_2$. i.e., 0.1-0.2, are significantly lower than the intensity values of region $R_1$ (shown in FIG. 5), i.e., 0.5-0.7.

Referring to FIGS. 2 through 7, in sensor assembly 102, NQR signals induced in second coil 116, i.e. the reference coil, are significantly smaller than those induced in first coil 114, i.e., the active sensor coil. The NQR signals are linearly polarized in a direction of an excitation RF field vector (not shown), i.e., $B_{1E}$, as induced by first coil 114. Also, the induced NQR signal in active sensor coil 114 is proportional to a scalar product of induced spin magnetization (which is aligned with excitation RF field vector $B_{1E}$) and a unit field vector (not shown), i.e., $B_{1R}$, produced by active sensor coil 114, i.e., the scalar product of $B_{1R}*B_{1E}$. Therefore, the NQR signal is relatively quite strong in active sensor coil 114 because $B_1R$ is parallel to $B_{1E}$ and the combined effect is additive in nature. Moreover, the NQR signals induced in active sensor coil 114 are located at or near the region of highest sensitivity of coil 114. In contrast, even though the NQR signals induced in reference coil 116 are located at or near the region of highest sensitivity of coil 116, the intensities of such signals are much smaller than those induced by active sensor coil 114. Therefore, the NQR signal as sensed by coil 116 is relatively weak and can be neglected. As such, even under those circumstances where the $B_1$ and $B_2$ field distributions of both active sensor coil 114 and reference coil 116 are substantially identical, active sensor coil 114 picks up most of the NQR signal while reference coil 116 detects little NQR signal, and the RFI measured by reference coil 116 may be subtracted from the signals sensed by active sensor coil 114 without any significant loss of NQR signal as sensed by coil 114.

Referring to FIGS. 1, 2, and 3, coils 114 and 116 are connected to independent receive amplifiers, such as RX amplifier 122 and RX1 amplifier 126, respectively. More specifically, first coil 114 is coupled to RX amplifier 122 through TX/RX switch 120, and TX amplifier 118 is coupled to TX/RX switch 120. TX amplifier 118 is configured to receive pulsed signals STX(t) (t represents time) from spectrometer 108 and transmit pulsed signals STX(t) to TX/RX switch 120. In a transmit mode, TR/RX switch 120 is configured to transmit pulses to first coil 114 through TX/RX switch 120. First coil 114 is configured to generate transmitted RF signals (not shown) toward target sample 125 (only shown in FIG. 3). The transmitted RF signals are substantially representative of pulsed signals STX(t). TX/RX switch 120 is also configured to change a mode of first coil 114 from a transmit mode to a receive mode to transmit the radiofrequency (RF) signals and receive return RF signals (not shown) from target sample 125.

Second coil 116 is coupled to RX1 amplifier 126 through RX switch 124. As such, second coil 116 receives RF signals (not shown) but does not transmit RF signals 130. In the exemplary embodiment, second coil 116 receives the background or environmental RF signals and generates and transmits reference signals Sn(t) that are substantially representative of background RF, e.g., interference (RFI) signals. n is an integer representing which member of a plurality of reference coils, if more than one is used, is receiving the background RF signals. In the exemplary embodiment, only one reference coil, i.e., second coil 116 is shown in the exemplary embodiment. Therefore, Sn(t) is represented as S1(t). Second coil 116 receives the background RF signals and generates and transmits first reference signals S1(t). Because second coil 116 only receives the background RF signals, second coil 116 is configured as the reference coil that samples background RFI. When sensor assembly 102 includes more than one reference coil, control circuitry 104 includes a reference receive (RXN) amplifier and a receive (RX) switch for each reference coil (discussed further below).

To facilitate receiving the return RF signals from target sample 125 at first coil 114 and the background RFI signals at second coil 116, target sample 125 is placed closer to active sensor coil 114 during scanning (as shown in FIG. 3). More specifically, target sample 125 is positioned at least partially within sensitive region $R_1$ generated about active sensor coil 114. Housing 112 may include an indication on a surface thereof (neither shown) to facilitate positioning active sensor coil 114 nearer to target sample 125 than reference coil 116 is to target sample 125. The indication may include markings or imprinting on the surface of housing 112 to indicate where to position detection system 100 with respect to target sample 125.

In the exemplary embodiment, sensor signal Sq(t) includes a quadrupole resonance (NQR) component Xq(t), an interference component I(t), and a noise component N(t) (only Sq(t) shown in FIGS. 1 and 2). As such, $S_q(t)=X_q(t)+I(t)+N(t)$, where NQR component Xq(t) is substantially representative of the return RF signals from target sample 125, interference component I(t) is substantially representative of the background RFI signals surrounding target sample 125 and/or detection system 100, and noise component N(t) represents RF signals (not shown) from intrinsic noise, such as thermal noise. i.e., electrical noise caused by thermal agitation of conducting electrons. Each reference signal Sn(t) includes an interference component In(t) and a noise signal Nn(t). As such, $S_n(t)=I_n(t)+N_n(t)$, where interference component In(t) represents RF signals from background RFI signals and Nn(t) represents RF signals from intrinsic noise. In the exemplary embodiment, reference coil 116 receives first reference signals S1(t) that includes an interference component I1(t) and a noise component N1(t) such that $S_1(t)=I_1(t)+N_1(t)$. Because only one reference coil 116 is shown in FIGS. 1-3, reference signals S1(t) are referred to below. However, sensor assembly 102 may include more than one reference coil for acquiring more than one reference signal (discussed further below).

Correction unit 106 receives sensor signals Sq(t) from RX amplifier 122 and reference signals S1(t) from RX1 amplifier 126. Correction unit 106 is configured to correct sensor signals Sq(t) using reference signals S1(t) to facilitate reducing or removing interference component I(t) from sensor signals Sq(t) (as described in more detail below). Correction unit 106 generates and transmits a corrected signals S(t) to spectrometer 108 and/or control unit 110 for further processing. When correction unit 106 is within spectrometer 108, spectrometer 108 generates and transmits corrected signals S(t) to control unit 110 for further processing. Spectrometer 108 and/or control unit 110 determines if a particular material, compound, and/or element is present in target sample 125 based on corrected signals S(t).

Figure 8:
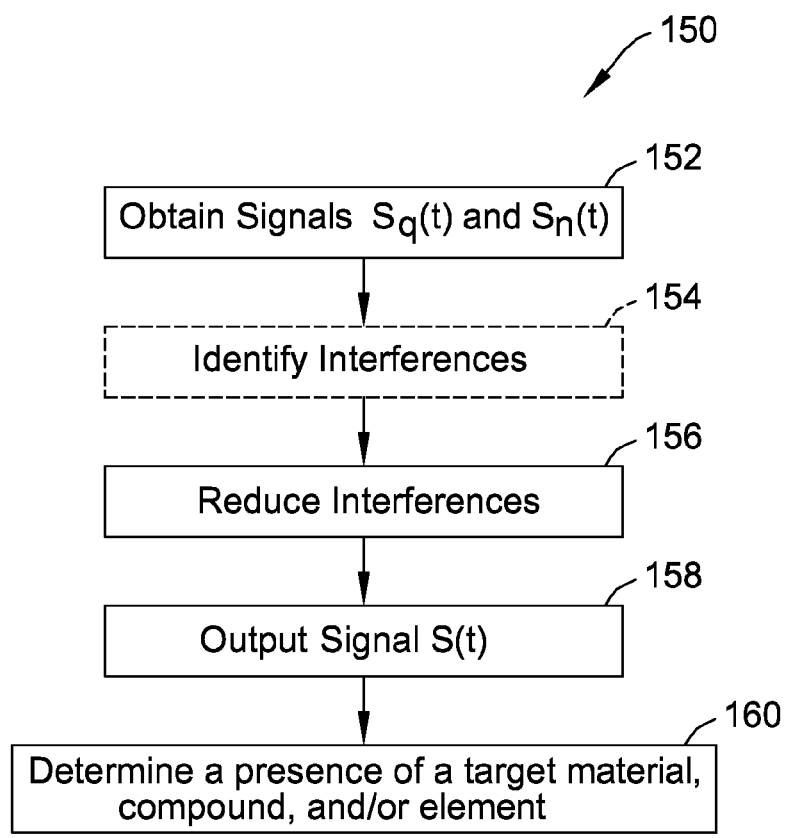

FIG. 8 shows a flowchart of a method 150 for using detection system 100 (shown in FIGS. 1-3). Method 150 may be used to determine if a target material, compound, and/or element is present in a sample and/or an object, such as target sample 125 (shown in FIG. 3). Method 150 is implemented based on NQR techniques using detection system 100. Referring to FIGS. 1-3 and FIG. 8, method 150 includes positioning detection system 100 near target sample 125 to receive NQR signals from target sample 125. Sensor signals Sq(t) and reference signals S1(t) are obtained 152 by scanning target sample 125 with the transmitted RF signals. More specifically, spectrometer 108 transmits pulsed signals STX(t) to TX amplifier 118 that transmits amplified pulsed signals STX(t) to TX/RX switch 120 that is configured such that first coil 114 is in the transmit mode. First coil 114 transmits the RF signals substantially representative of pulsed signals STX(t) to target sample 125. Then, the configuration of TX/RX switch 120 is shifted from the transmit mode to the receive mode such that first coil 114 is also shifted to the receive mode, and first coil 114 receives the return RF signals from target sample 125 to generate and transmit 152 sensor signals Sq(t). To obtain 152 reference signals S1(t), RX switch 124 is configured such that second coil 116 receives the background RF signals and not the return RF signals from target sample 125. Receipt of the return RF signals by first coil 114 and receipt of the background RF signals is substantially simultaneous.

Interferences in sensor signals Sq(t) and/or reference signals S1(t) may be identified 154 before the interferences are removed and/or reduced 156. The identification step 154 may be omitted or included in method 150 based on which correction algorithm is used in the reduction step 156 (as described further below). In the exemplary embodiment, the interferences are identified 154 using any suitable method and/or technique. For example, a detection algorithm, such as an energy detector, may be applied for a binary decision problem of detecting a presence of signals in noise.

The interferences are removed and/or reduced 156 from sensor signals Sq(t) using at least one reference signals Sn(t), such as first reference signals S1(t), to generate a corrected signals S(t). Corrected signals S(t) includes NQR component Xq(t), a modified interference component $\tilde{I}(t)$, and a modified noise component $\tilde{N}(t)$ such that $S(t)=X_q(t)+\tilde{I}(t)+\tilde{N}(t)$. The interferences may be mitigated and/or removed 156 using any suitable method and/or technique that removes and/or reduces interference component I(t) of sensor signals Sq(t) such that modified interference component $\tilde{I}(t)$ is about equal to zero. As such, reduction step 156 may be referred to as RFI mitigation and/or RFI correction.

RFI mitigation may be accomplished using at least two different algorithms. In a first algorithm, reduction 156 includes coherent subtraction of background RFI signals (i.e., interference component I(t)) from sensor signals Sq(t) using adaptive linear regression. The quality of output of such an algorithm increases as a sensitivity of reference coil 116 increases because degradation of a signal-to-noise ratio (SNR) in sensor signals Sq(t) is lessened as the sensitivity of reference coil 116 increases. A correction unit (not shown in FIG. 1-3 or 8 and discussed further below) is configured to execute the first algorithm.

Figure 10:
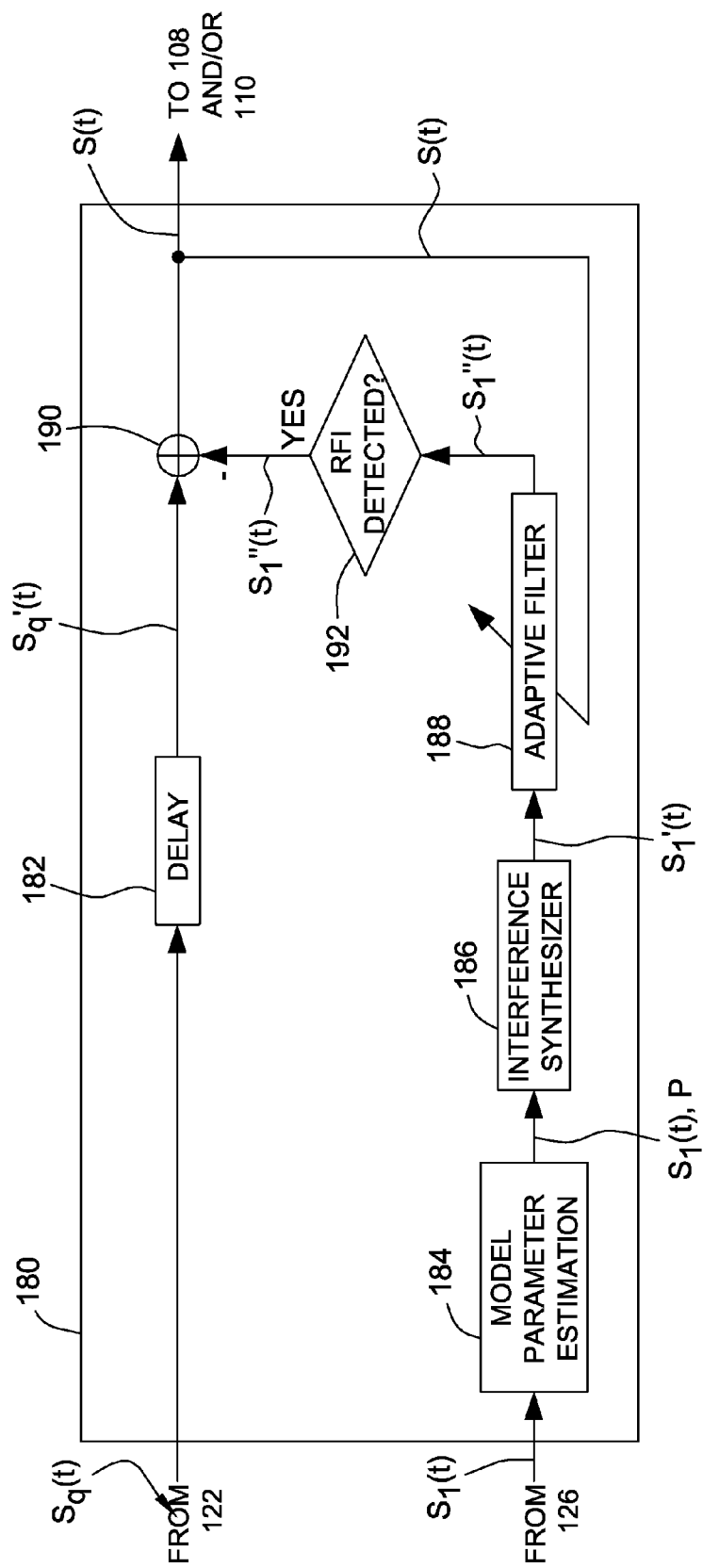

In a second algorithm, reduction 156 includes using reference signals S1(t) from reference coil 116 to estimate RFI waveforms followed by coherent subtraction. This estimation/subtraction approach uses an estimated, noise-free-RFI-waveforms version of the background RFI signals that may then be coherently subtracted from sensor signals Sq(t) without degradation in SNR. FIG. 10 shows a correction unit 180 configured to perform the second algorithm. Correction unit 180 is described in more detail below. Correction algorithms in addition to, or as an alternative to, the first and second algorithms may be used to reduce 156 interference from sensor signals Sq(t) using at least one reference signal Sn(t).

Method 150 further includes generating and transmitting 158 corrected signals S(t) from correction unit 106 to spectrometer 108 and/or control unit 110 for further processing to determine if the target material, compound, and/or element is present in target sample 125. Corrected signals S(t) may be processed using any suitable method and/or technique to determine 160 the presence of the target material, compound, and/or element based on corrected signals S(t). In the absence of interferences, a conventional NQR signal analysis is performed. More specifically, another energy detector is applied to determine a presence of an NQR signal and if an energy of the NQR signal is above a predetermined threshold, an "alarm" indication is output and if the energy of the NQR signal is below the threshold a "clear" indication is output.

Figure 9:
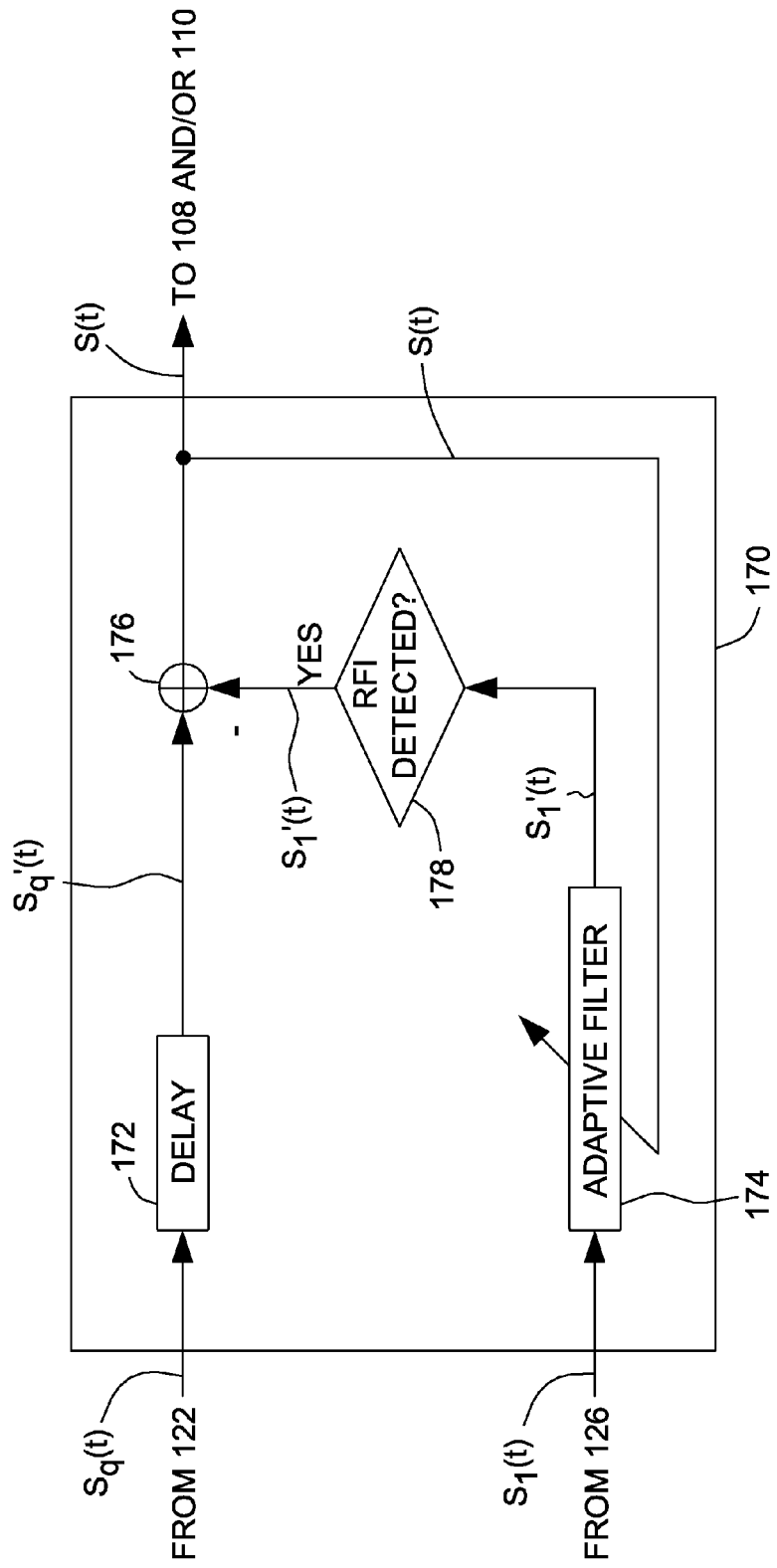

FIG. 9 is a schematic view of an exemplary correction unit 170 for use with detection system 100 (shown in FIGS. 1-3) as correction unit 106 (shown in FIG. 1). Correction unit 170 is configured to execute a correction and/or cancellation algorithm. In the exemplary embodiment, correction unit 170 is configured to execute an adaptive mitigation algorithm for cancellation of RFI background from sensor signals Sq(t) to generate corrected signals S(t). Correction unit 170 includes a delay circuit 172, a filter circuit 174, and a subtraction circuit 176. Delay circuit 172 is in communication with RX amplifier 122 (shown in FIGS. 1 and 2) to receive sensor signals Sq(t), and filter circuit 174 is in communication with RX1 amplifier 126 (shown in FIGS. 1 and 2) to receive reference signals S1(t). Subtraction circuit 176 is in communication with delay circuit 172 and filter circuit 174. Subtraction circuit 176 is also in communication with NQR spectrometer 108 and/or control unit 110 (both shown in FIG. 1).

Delay circuit 172 is configured to delay sensor signals Sq(t) to compensate for time domain differences between sensor signals Sq(t) and reference signals S1(t). As such, delay circuit 172 generates and transmits delayed sensor signals Sq'(t) to subtraction circuit 176. Filter circuit 174 is configured as an adaptable filter that matches interferences in sensor signals Sq(t) and reference signals S1(t). More specifically, first coil 114 and second coil 116 (both shown in FIGS. 1 and 2) may have different gains, which will cause sensor signals Sq(t) and reference signals S1(t) to have different amplitudes. Filter circuit 174 is configured to compensate for the differences in amplitudes of sensor signals Sq(t) and reference signals S1(t) and generate and transmit filtered reference signals S1'(t). Subtraction circuit 176 is configured to subtract filtered reference signals S1'(t) from delayed sensor signals Sq'(t). To adapt to real-time signal differences, filter circuit 174 receives feedback from subtraction circuit 176.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Correction unit 170 includes a decision circuit 178 that determines if RFI is present in filtered reference signals S1'(t). If RFI is present, decision circuit 178 transmits filtered reference signals S1'(t) to subtraction circuit 176. If RFI is not present, filtered reference signals S1'(t) are not subtracted from delayed sensor signals Sq'(t) such that delayed sensor signals Sq'(t) are not corrected unless RFI is present. Identification or detection of interferences prior to applying the cancellation algorithm enables the RFI suppression algorithm to not be applied if interferences do not exist. In the absence of interferences, adaptive filtering may attempt to remove a portion of the signal of interest or degrade the signal-to-noise ratio (SNR).

In operation, sensor signals Sq(t) are transmitted from RX amplifier 122 to delay circuit 172 that generates and transmits delayed sensor signals Sq'(t) to subtraction circuit 176 to compensate for time domain differences between sensor signals Sq(t) and reference signals S1(t). Reference signals S1(t) are transmitted from RX1 amplifier 126 to filter circuit 174 to adaptively compensate for any differences in amplitudes of sensor signals Sq(t) and reference signals S1(t) that may be representative of different gains between first coil 114 and second coil 116. Filter circuit 174 generates and transmits filtered reference signals S1'(t) to decision circuit 178 that determines if RFI is present in filtered reference signals S1'(t). If RFI is present, decision circuit 178 transmits filtered reference signals S1'(t) to subtraction circuit 176. If RFI is not present, filtered reference signals S1'(t) are not transmitted to subtraction circuit 176.

As described above, subtraction circuit 176 is configured to subtract filtered reference signals S1'(t) from delayed sensor signals Sq'(t) when RFI is present as determined by decision circuit 178. Subtraction of filtered reference signals S1'(t) from delayed sensor signals Sq'(t) through subtraction circuit 176 facilitates reducing and/or substantially eliminating interference component I(t) from delayed sensor signals Sq'(t) to generate a modified interference component $\tilde{I}(t)$. Subtraction of filtered reference signals S1'(t) from delayed sensor signals Sq'(t) also generates a modified noise component $\tilde{N}(t)$.

Also, in operation, for those situations when RFI is not present as determined by decision circuit 178, filtered reference signals S1'(t) are not transmitted to subtraction circuit 176. Therefore, filtered reference signals S1'(t) are not subtracted from delayed sensor signals Sq'(t) such that delayed sensor signals Sq'(t) are not corrected unless RFI is present. Identification or detection of interferences prior to applying the cancellation algorithm enables the RFI suppression algorithm to not be applied if interferences do not exist. Also, in the absence of interferences, a potential for removing a portion of the signal of interest or degrading the SNR is reduced.

Therefore, subtraction circuit 176 generates and transmits corrected signals S(t) to NQR spectrometer 108 and/or control unit 110 for further processing. For ease of discussion, signals S(t) are described as "corrected", whether or not filtered reference signals S1'(t) are subtracted from delayed sensor signals Sq'(t). Corrected signals S(t) are also transmitted to filter circuit 174 as feedback signals.

Correction unit 170 is shown and described in the exemplary embodiment as enabled in hardware. Alternatively, correction unit 170, in its entirety or portions thereof, may also be enabled in a software application.

FIG. 10 is a schematic view of an alternative exemplary correction unit 180 for use with detection system 100 (shown in FIGS. 1-3) as correction unit 106 (shown in FIG. 1). Correction unit 180 is configured to execute a correction and/or cancellation algorithm. In the exemplary embodiment, correction unit 180 is configured to perform an estimation/subtraction algorithm for cancellation of RFI background from sensor signals Sq(t) to generate corrected signals S(t). Correction unit 180 includes a delay circuit 182, an estimation circuit 184, a synthesizer circuit 186, a filter circuit 188, and a subtraction circuit 190. Delay circuit 182 is in communication with RX amplifier 122 (shown in FIGS. 1 and 2) to receive sensor signals Sq(t), and estimation circuit 184 is in communication with RX1 amplifier 126 (shown in FIGS. 1 and 2) to receive reference signals S1(t). Synthesizer circuit 186 is in communication with estimation circuit 184, and filter circuit 188 is in communication with synthesizer circuit 186. Subtraction circuit 190 is in communication with delay circuit 182 and filter circuit 188. Subtraction circuit 190 is also in communication with NQR spectrometer 108 and/or control unit 110 (both shown in FIG. 1).

Delay circuit 182 is configured to delay sensor signals Sq(t) to compensate for time domain differences between sensor signals Sq(t) and reference signals S1(t). As such, delay circuit 182 generates and transmits delayed sensor signals Sq'(t) to subtraction circuit 190. Estimation circuit 184 is configured as a model parameter estimator that estimates interference in reference signals S1(t). More specifically, estimation circuit 184 estimates interference parameters P to facilitate modeling RFI interference. Synthesizer circuit 186 is configured as an interference synthesizer that generates and transmits synthesized reference signals S1'(t) having an interference component based on the estimated interference parameters P from estimation circuit 184. Synthesized reference signals S1'(t) are transmitted from synthesizer circuit 186 to filter circuit 188.

Filter circuit 188 is configured as an adaptable filter that matches interferences in sensor signals Sq(t) and synthesized reference signals S1'(t). More specifically, first coil 114 and second coil 116 (both shown in FIGS. 1 and 2) may have different gains, which will cause sensor signals Sq(t) and reference signals S1(t) to have different amplitudes. Filter circuit 188 is configured to compensate for the differences in amplitudes of sensor signals Sq(t) and synthesized reference signals S1'(t) and generate and transmit filtered reference signals S1'(t). Subtraction circuit 190 is configured to subtract filtered reference signals S1'(t) from delayed sensor signals Sq'(t). To adapt to signal differences, filter circuit 188 receives feedback from subtraction circuit 190.

Correction unit 180 includes a decision circuit 192 that determines if RFI is present in filtered reference signals S1"(t). If RFI is present, decision circuit 192 transmits filtered reference signals S1"(t) to subtraction circuit 190. If RFI is not present, filtered reference signals S1"(t) are not subtracted from delayed sensor signals Sq'(t) such that delayed sensor signals Sq'(t) are not corrected unless RFI is present. Identification or detection of interferences prior to applying the cancellation algorithm enables the RFI suppression algorithm to not be applied if interferences do not exist. As discussed above with respect to FIG. 9, the cancellation algorithm may not be applied if interferences are not detected in the signals.

In operation, sensor signals Sq(t) are transmitted from RX amplifier 122 to delay circuit 182 that generates and transmits delayed sensor signals Sq'(t) to subtraction circuit 190 to compensate for time domain differences between sensor signals Sq(t) and reference signals S1(t). Reference signals S1(t) are transmitted from RX1 amplifier 126 to estimation circuit 184 to estimate interference parameters P to facilitate modeling RFI interference. Reference signals S1(t) are transmitted from estimation circuit 184 to synthesizer circuit 186 that generates and transmits synthesized reference signals S1'(t) having an interference component based on the estimated interference parameters P from estimation circuit 184. Synthesized reference signals S1'(t) are transmitted from synthesizer circuit 186 to filter circuit 188 to adaptively compensate for any differences in amplitudes of sensor signals Sq(t) and reference signals S1(t) that may be representative of different gains between first coil 114 and second coil 116. Filter circuit 188 generates and transmits filtered reference signals S1'(t) to decision circuit 192 that determines if RFI is present in filtered reference signals S1'(t). If RFI is present, decision circuit 192 transmits filtered reference signals S1'(t) to subtraction circuit 190. If RFI is not present, filtered reference signals S1'(t) are not transmitted to subtraction circuit 190.

As described above, subtraction circuit 190 is configured to subtract filtered reference signals S1"(t) from delayed sensor signals Sq'(t) when RFI is present as determined by decision circuit 192. Subtraction of filtered reference signals S1"(t) from delayed sensor signals Sq'(t) through subtraction circuit 190 facilitates reducing and/or substantially eliminating interference component I(t) from delayed sensor signals Sq'(t) to generate a modified interference component Ĩ(t). Subtraction of filtered reference signals S1"(t) from delayed sensor signals Sq'(t) also generates a modified noise component Ñ(t).

Also, in operation, for those situations when RFI is not present as determined by decision circuit 192, filtered reference signals S1"(t) are not transmitted to subtraction circuit 190. Therefore, filtered reference signals S1"(t) are not subtracted from delayed sensor signals Sq'(t) such that delayed sensor signals Sq'(t) are not corrected unless RFI is present. Identification or detection of interferences prior to applying the cancellation algorithm enables the RFI suppression algorithm to not be applied if interferences do not exist.

Therefore, subtraction circuit 190 generates and transmits corrected signals S(t) to NQR spectrometer 108 and/or control unit 110 for further processing. For ease of discussion, signals S(t) are described as "corrected", whether or not filtered reference signals S1"(t) are subtracted from delayed sensor signals Sq'(t). Corrected signals S(t) are also transmitted to filter circuit 188 as feedback signals.

Correction unit 180 is shown and described in the exemplary embodiment as enabled in hardware. Alternatively, correction unit 180, in it's entirety or portions thereof, may also be enabled in a software application.

Figure 11:
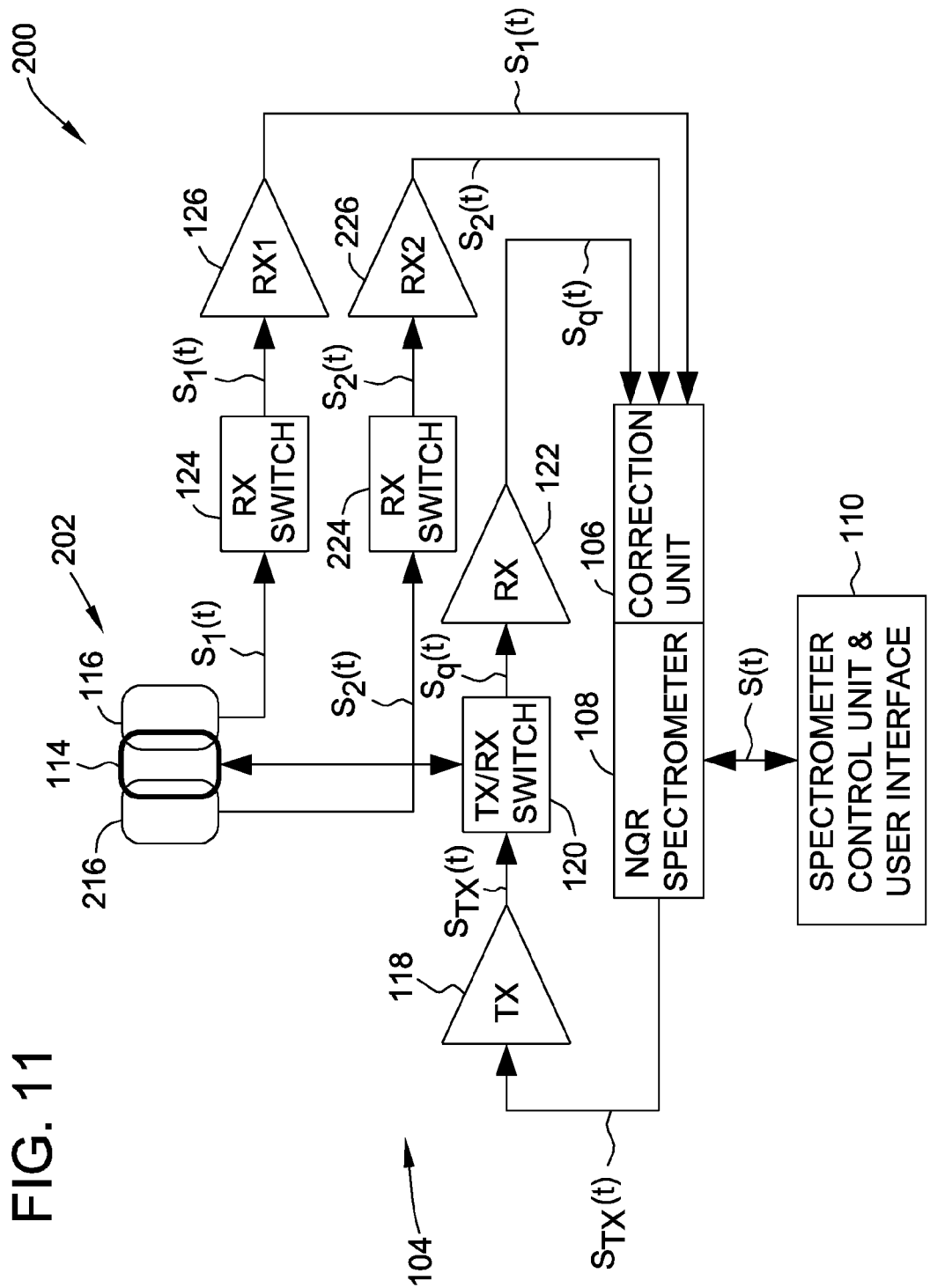
Figure 12:
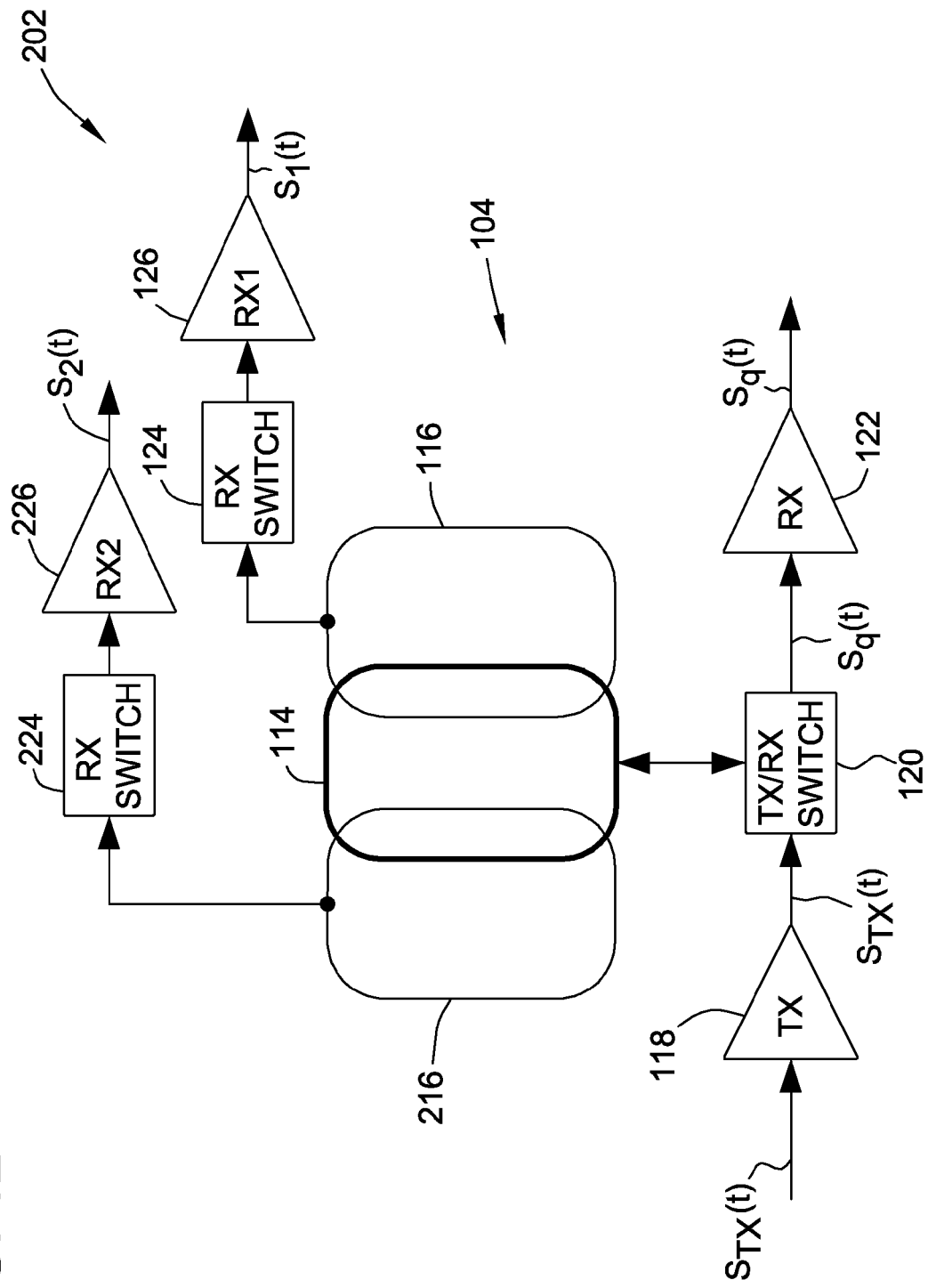

FIG. 11 is a schematic view of a first alternative exemplary detection system 200. FIG. 12 is a schematic view of a first alternative exemplary sensor assembly 202 for use with detection system 200. Detection system 200 is substantially similar to detection system 100 (shown in FIGS. 1-3), with the exception that detection system 200 includes sensor assembly 202 having a third coil 216. As such, components shown in FIGS. 11 and 12 are labeled with the same reference numbers used in FIGS. 1-3. In the exemplary embodiment shown in FIGS. 11 and 12, third coil 216 overlaps first coil 114 such that mutual inductance between third coil 216 and first coil 114 is substantially reduced for the reasons discussed above for sensor assembly 102 (shown in FIGS. 1-3).

Third coil 216 is a second reference coil that is coupled to a second receive (RX2) amplifier 226 through a second receive (RX) switch 224 such that third coil 216 receives the background RF signals but does not transmit the RF signals. RX1 amplifier 126 and RX2 amplifier 226 are configured to reduce and/or cancel mutual inductance between second coil 116 and third coil 216. In the exemplary embodiment, third coil 216 receives the background or environmental RF signals and generates and transmits reference second reference signals S2(t). Second reference signals S2(t) include an interference component I2(t) and a noise signal component N2(t). As such, $S_2(t)=I_2(t)+N_2(t)$, where interference component I2(t) represents the background RFI signals and N2(t) represents RF signals from intrinsic noise as described above for N1(t).

As described above for sensor assembly 102, in the exemplary embodiment, sensor assembly 202 is a phased-coil array configured to eliminate mutual inductance between coils 114, 116, and 216. More specifically, first coil 114 overlaps second coil 116 and third coil 216 by an amount that substantially reduces mutual inductance between coils 114, 116, and 216.

Correction unit 106 is configured to receive second reference signals S2(t) from RX2 amplifier 226. As such, correction unit 106 uses first reference signals S1(t) and second reference signals S2(t) to correct sensor signals Sq(t), as described in more detail above. When correction unit 170 (shown in FIG. 9) is used as correction unit 106, and there is more than one reference coil, filter circuit 174 receives all of the reference signals S1(t), S2(t), . . . Sn(t). The reference signals may be combined to provide a combined reference signal with improved SNR, or the reference signals may be processed separately. When correction unit 180 (shown in FIG. 10) is used as correction unit 106, and there is more than one reference coil, estimation circuit 184 receives all of the reference signals S1(t), S2(t), . . . Sn(t). The reference signals are then combined or processed separately.

FIGS. 13-16 show alternative sensor assemblies for use with detection system 100 (shown in FIGS. 1-3) and/or detection system 200 (shown in FIG. 11). Although only one coil in each of FIGS. 13-16 is indicated as being an active sensor coil, more than one coil per sensor assembly may be active sensor coils with the remaining coils being reference coils.

Figure 13:
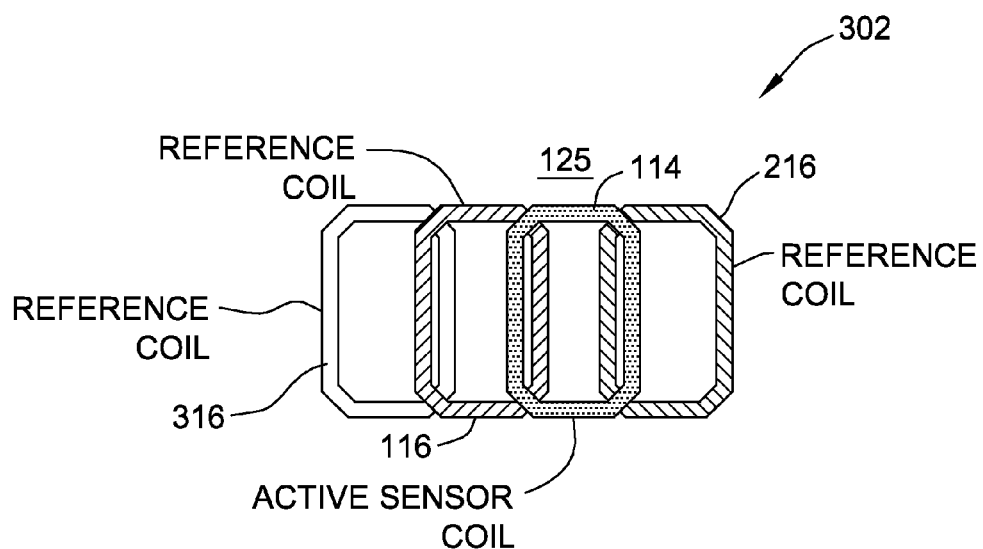

FIG. 13 is a schematic view of a second alternative exemplary sensor assembly 302 for use with detection system 100 (shown in FIGS. 1-3) and/or detection system 200 (shown in FIG. 11). Sensor assembly 302 includes more than three coils where at least one coil is the active sensor coil (similar to active sensor coil 114 (shown in FIGS. 1-3, 11, and 12)) and the other coils are reference coils (similar to reference coil 116 (shown in FIGS. 1-3)) or reference coil 216 (shown in FIGS. 11 and 12).

In this alternative exemplary embodiment, sensor assembly 302 is substantially similar to sensor assembly 202 (shown in FIGS. 12 and 13), with the exception that sensor assembly 302 includes a fourth coil 316. As such, components shown in FIGS. 11 and 12 are labeled with the same reference numbers used in FIGS. 12 and 13.

As described above for sensor assemblies 102 (shown in FIGS. 1-3) and 202, in this alternative exemplary embodiment, sensor assembly 302 is a phased-coil array configured to eliminate mutual inductance between coils 114, 116, 216, and 316. More specifically, first coil 114 overlaps second coil 116 and third coil 216 by an amount that substantially reduces mutual inductance between coils 114, 116, and 216. Also, second coil 116 overlaps fourth coil 316 such that mutual inductance between second coil 116 and fourth coil 316 is substantially reduced for the reasons discussed above with respect to sensor assembly 102.

Circuitry similar to that for detection system 200 (shown in FIGS. 11 and 12) is used with the exceptions that, e.g., and without limitation, a third receive amplifier (not shown) similar to receive amplifiers 126 and 226 (both shown in FIGS. 11 and 12) and a third receive switch (not shown) similar to receive switches 124 and 224 (both shown in FIGS. 11 and 12) are coupled to fourth coil 316 such that fourth coil 316 receives the background RF signals but does not transmit the RF signals. Operation of sensor assembly 302 is similar to that described above for sensor assemblies 102 and 202.

Also, this alternative exemplary embodiment, sensor assembly 302 is shown in a substantially horizontal orientation. Alternatively, sensor assembly 302 may have any orientation that enables operation of sensor assembly 302 and detection systems 100 and 200 as described herein, including, without limitation, substantially vertical.

Figure 14:
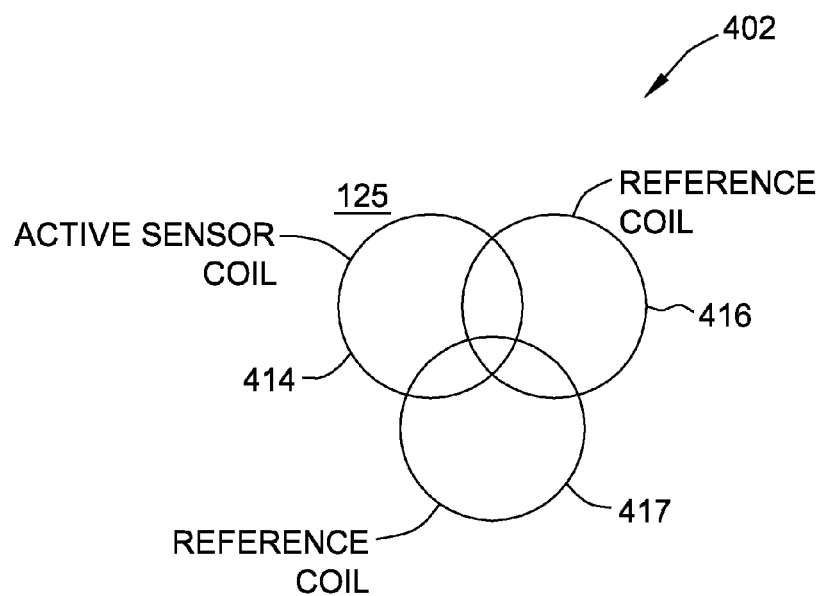

FIG. 14 is a schematic view of a third alternative exemplary sensor assembly 402 for use with detection system 100 (shown in FIGS. 1-3) and/or detection system 200 (shown in FIG. 11). Sensor assembly 402 includes three coils where at least one coil is the active sensor coil 414 (similar to active sensor coil 114 (shown in FIGS. 1-3, 11, and 12)) and the other coils are reference coils 416 and 417 (similar to reference coil 116 (shown in FIGS. 1-3) and reference coil 216 (shown in FIGS. 11 and 12)).

In this alternative exemplary embodiment, sensor assembly 402 is substantially similar to sensor assembly 202 (shown in FIGS. 11 and 12), with the exception that sensor assembly 402 includes substantially circular interlocking coils 414, 416, and 417. Circuitry similar to that for detection system 200 (shown in FIGS. 11 and 12) is used. Operation of sensor assembly 402 is similar to that described above for sensor assemblies 102 (shown in FIGS. 1-3) and 202.

As described above for sensor assemblies 102, 202, and 302 (shown in FIG. 13), in this alternative exemplary embodiment, sensor assembly 302 is a phased-coil array configured to eliminate mutual inductance between interlocking coils 414, 416, and 417. More specifically, active sensor coil 414 and reference coils 416 and 417 overlap each other by an amount that substantially reduces mutual inductance between coils 414, 416, and 417 as described above for sensor assembly 102.

Figure 15:
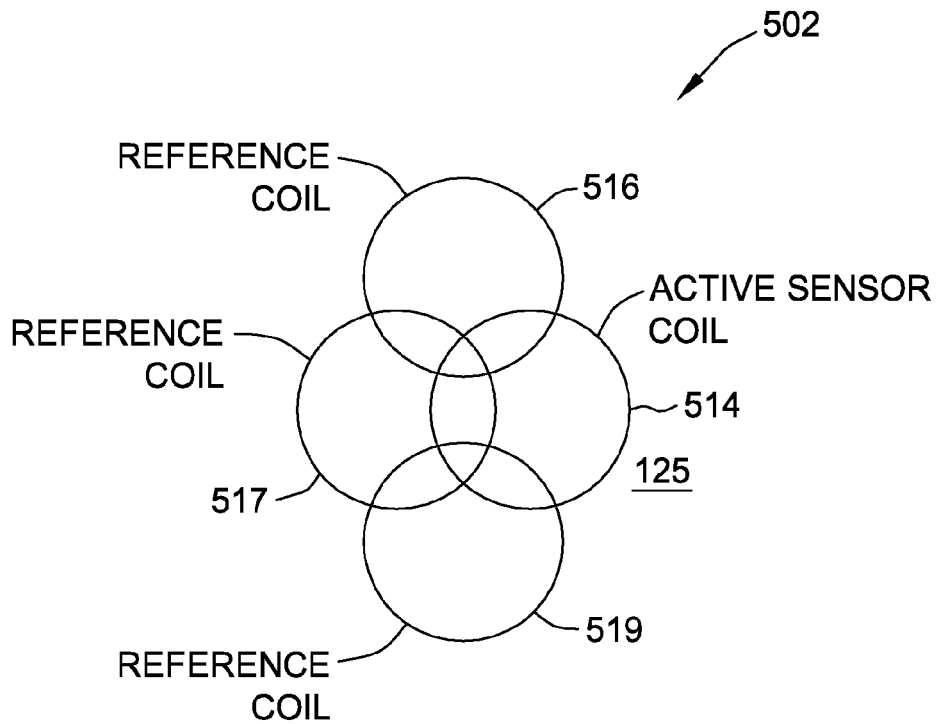

FIG. 15 is a schematic view of a fourth alternative exemplary sensor assembly 502 for use with detection system 100 (shown in FIGS. 1-3) and/or detection system 200 (shown in FIGS. 11 and 12). Sensor assembly 502 includes more than three coils where at least one coil is the active sensor coil 514 (similar to active sensor coil 114 (shown in FIGS. 1-3, 11, and 12)) and the other coils are reference coils 516, 517, and 519 (similar to reference coil 116 (shown in FIGS. 1-3)) and reference coil 216 (shown in FIGS. 11 and 12).

In this alternative exemplary embodiment, sensor assembly 502 is substantially similar to sensor assembly 402 (shown in FIG. 14), with the exception that sensor assembly 502 includes four substantially circular interlocking coils 514, 516, 517, and 519. Circuitry similar to that for detection system 200 is used with the exceptions that, e.g., without limitation, a third receive amplifier and third receive switch (neither shown) coupled to fourth coil 519 such that fourth coil 519 receives the background RF signals but does not transmit RF signals 130 (shown in FIG. 3). Operation of sensor assembly 502 is similar to that described above for sensor assemblies 102 (shown in FIGS. 1-3) and 202 (shown in FIGS. 11 and 12).

As described above for sensor assemblies 102 (shown in FIGS. 1-3), 202 (shown in FIGS. 11 and 12), 302 (shown in FIG. 13), and 402 (shown in FIG. 14), in this alternative exemplary embodiment, sensor assembly 502 is a phased-coil array configured to eliminate mutual inductance between coils 514, 516, 517, and 519. More specifically, active sensor coil 514 overlaps reference coils 516, 517, and 519 by an amount that substantially reduces mutual inductance between coils 514, 516, 517, and 519 as described above for sensor assembly 102.

Figure 16:
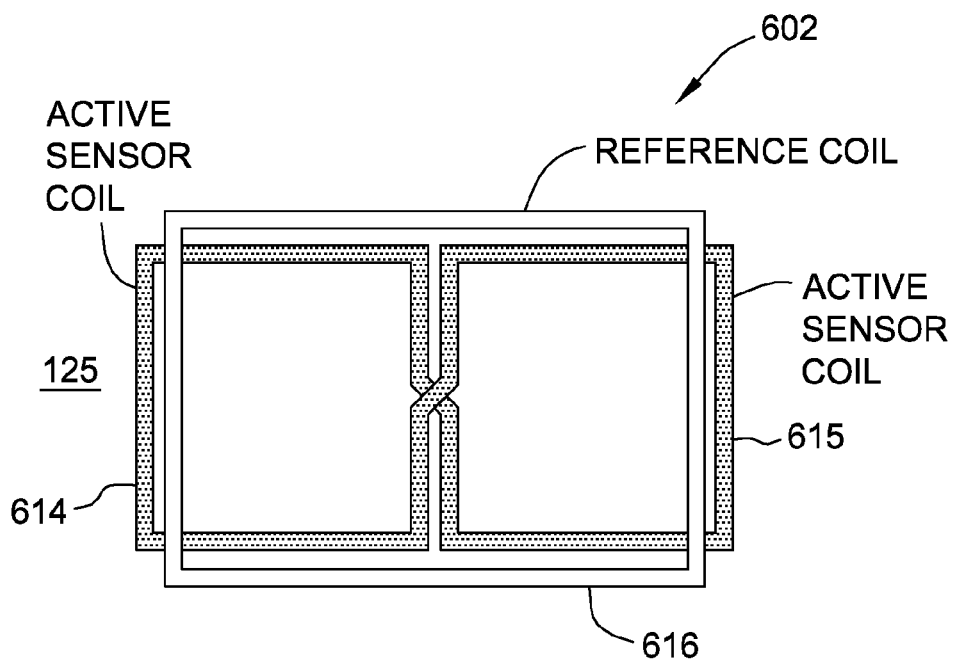

FIG. 16 is a schematic view of a fourth alternative exemplary sensor assembly 602 for use with detection system 100 (shown in FIGS. 1-3) and/or detection system 200 (shown in FIG. 11). Sensor assembly 602 includes three coils where two of the coils are coupled active sensor coils 614 and 615 (similar to active sensor coil 114 (shown in FIGS. 1-3, 11, and 12)) and the other coil is a reference coils (similar to reference coil 116 (shown in FIGS. 1-3)) and reference coil 216 (shown in FIGS. 11 and 12).

In this alternative exemplary embodiment, reference coil 616 is substantially rectangular in shape and overlaps active sensor coils 614 and 615 in a manner similar to that for active sensor coil 114 and reference coil 116 such that at least a portion of coils 614 and 615 may be placed closer to target sample 125 than reference coil 616.

Circuitry similar to that for detection system 100 is used with the exceptions that, e.g., and without limitation, a second TX amplifier (not shown) similar to TX amplifier 118 (shown in FIGS. 1 and 2), a second TX/RX switch (not shown) similar to RX/TX switch 120, and a second RX amplifier (not shown) similar to RX amplifier 122 (shown in FIGS. 1 and 2) are coupled to active sensor coil 615 such that active sensor coil 615 transmits RF signals 130 (shown in FIG. 3) and receives the return RF signals. Operation of sensor assembly 602 is similar to that described above for sensor assemblies 102 (shown in FIGS. 1-3) and 202 (shown in FIGS. 11 and 12).

As described above for sensor assemblies 102 (shown in FIGS. 1-3), 202 (shown in FIGS. 11 and 12), 302 (shown in FIG. 13), 402 (shown in FIGS. 14), and 502 (shown in FIG. 15), in this alternative exemplary embodiment, sensor assembly 602 is a phased-coil array configured to eliminate mutual inductance between coils 614, 615, and 616. More specifically, reference coil 616 overlaps active sensor coils 614 and 615 by an amount that substantially reduces mutual inductance between coils 614, 615, and 616 as described above for sensor assembly 102.

The detection systems described herein include a NQR sensor having multiple closely-spaced (i.e., co-located) surface coils in a phased-coil array that simultaneously receive NQR responses from a sample and external RFI. In the exemplary embodiment, all the surface coils are tuned at an NQR resonance frequency of a sample of interest such that all channels receiving RF signals will be equivalents. In the phased-coil array, each coil in the array is positioned to have substantially no interaction with each adjacent coil, and interactions between non-adjacent surface coils are minimized by coupling each onto a low-impedance pre-amplifier.

At least one coil in the coil array is used to apply pulsed RF excitation to induce NQR responses from the target sample. This coil of the array is positioned closer to the interrogated sample than other coils in the array are. As such, the induced NQR responses are received by one or more coils of the phased-coil array. The external interference, such as RFI, that may corrupt the desired NQR signals is received by one or more other coils in the phased-coil array.

One RFI cancellation method described herein uses adaptive filtering for coherent mitigation of the RFI from the afflicted NQR data with minimum distortions in the underlying signals. The RFI cancellation algorithm may initially apply an algorithm to detect interferences before attempting to remove or reduce the interferences in the signals acquired by the active sensor coil. Such an identification step is used when there is an absence of external interferences. Otherwise, the adaptive filtering algorithm may attempt to remove a signal of interest or degrade a SNR of the signal of interest. Further, the external RFI received with multiple reference coils may be combined to enhance the SNR of the external interference signal and improve the performance of the cancellation algorithm. An alternative RFI cancellation method described herein uses estimation/subtraction algorithms and the reference signals from the reference coils to obtain a noise-free representation of the external RFI and subtract the noise-free representation from the NQR signal of interest.

Because the above-described embodiments include a main NQR coil (i.e., the active sensor coil) co-located with at least one reference antenna (i.e., the reference coil(s)), the systems described herein reduce a number of antennas used for sampling external RFI, reduce a footprint of the system, and/or improve measurement of the external interference by sampling background signals in the same region as the main NQR coil.

A technical effect of the systems and methods described herein includes at least one of: (a) obtaining a sensor signal from an active sensor coil and at least one reference signal from at least one reference coil; (b) reducing an interference component of the sensor signal using the at least one reference signal to generate a corrected signal; and (c) determining a presence of a target material based on the corrected signal.

Exemplary embodiments of nuclear quadrupole resonance detection systems and methods of using the same are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other RF applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A nuclear quadrupole resonance (NQR) sensor assembly comprising:
    an active sensor coil configured to transmit radiofrequency (RF) signals to an object of interest and receive return RF signals from the object of interest to generate sensor signals substantially representative of the return signals, said active sensor coil extending in a length-wise dimension and a height-wise dimension orthogonal to the length-wise dimension; and
    at least one reference coil extending in the length-wise dimension and the height-wise dimension and separated from said active sensor coil in a depth-wise dimension orthogonal to the length-wise and height-wise dimensions, said at least one reference coil thereby decoupled from said active sensor coil, said at least one reference coil configured to receive environmental RF signals to generate reference signals at least partially representative of the environmental RF signals, wherein the reference signals are used to reduce interference components within the return signals.

2. The NQR sensor assembly in accordance with claim 1, wherein said at least one reference coil is a plurality of said reference coils co-located with said active sensor coil, wherein said plurality of said reference coils and said active sensor coil are tuned to receive return RF signals within a frequency band defined by at least one resonant frequency of the object of interest.

3. The NQR sensor assembly in accordance with claim 2, wherein said plurality of reference coils comprises at least one of said reference coils positioned on each of opposite sides of said active sensor coil.

4. The NQR sensor assembly in accordance with claim 2, wherein said plurality of reference coils are at least partially overlapped a predetermined amount in the length-wise and height-wise dimensions that substantially reduces mutual inductance between said plurality of reference coils.

5. A nuclear quadrupole resonance (NQR) system comprising:
    an active sensor coil configured to transmit radiofrequency (RF) signals to an object of interest and receive return RF signals from the object of interest to generate sensor signals substantially representative of the return signals, said active sensor coil extending in a length-wise dimension and a height-wise dimension orthogonal to the length-wise dimension;
    at least one reference coil extending in the length-wise dimension and the height-wise dimension and separated from said active sensor coil in a depth-wise dimension orthogonal to the length-wise and height-wise dimensions, said at least one reference coil thereby decoupled from said active sensor coil, said at least one reference coil configured to receive environmental RF signals to generate reference signals at least partially representative of the environmental RF signals; and a correction unit in communication with said active sensor coil and said at least one reference coil, said correction unit configured to remove interference components from the sensor signal using the at least one reference signal.

6. The NQR system in accordance with claim 5 further comprising a transmit/receive switch configured to shift said active sensor coil between a receive mode of operation and a transmit mode of operation.

7. The NQR system in accordance with claim 5 further comprising an NQR spectrometer configured to transmit pulsed signals to said active sensor coil to facilitate the transmission of the RF signals.

8. The NQR system in accordance with claim 5, wherein said correction unit is configured to determine a presence of radiofrequency interference (RFI) in the environmental RF signals.

9. The NQR system in accordance with claim 5, wherein said correction unit is configured to generate a synthesized reference signal at least partially representative of the environmental RF signals and estimated interference parameters.

10. The NQR system in accordance with claim 5, wherein said at least one reference coil is a plurality of said reference coils co-located with said active sensor coil.

11. The NQR system in accordance with claim 10, wherein said plurality of reference coils comprises at least one of said reference coils positioned on each of opposite sides of said active sensor coil.

12. The NQR system in accordance with claim 5, wherein said at least one reference coil and said active sensor coil are tuned to receive return RF signals within a frequency band defined by at least one resonant frequency of the object of interest.

13. The NQR system in accordance with claim 5, wherein said active sensor coil is configured to be positioned closer to the object of interest than said at least one reference coil such that a sensitive volume is defined proximate the object of interest.

14. A method for performing nuclear quadrupole resonance (NQR) detection, said method comprising:

defining a linear phased-coil array comprising co-locating an active sensor coil with at least one reference coil such that the coils extend in a length-wise dimension and a height-wise dimension orthogonal to the length-wise dimension, wherein the at least one reference coil is separated from the active sensor coil in a depth-wise dimension orthogonal to the length-wise and height-wise dimensions, thereby decoupling the least one reference coil from the active sensor coil;

generating sensor signals from an active sensor coil and reference signals from at least one reference coil;

reducing an interference component of the sensor signals using the reference signals to generate corrected signals; and determining a presence of a target material based on the corrected signals.

15. The method in accordance with claim 14, wherein generating sensor signals from the active sensor coil comprises transmitting radiofrequency (RF) signals to the target material and receiving return RF signals from the target material to generate the sensor signals that are substantially representative of the return RF signals.

16. The method in accordance with claim 15 further comprising switching the active sensor coil between a receive mode of operation and a transmit mode of operation through operation of a transmit/receive switch.

17. The method in accordance with claim 14, wherein generating reference signals from at least one reference coil comprises receiving environmental RF signals to generate the reference signals that are at least partially representative of the environmental RF signals.

18. The method in accordance with claim 14, wherein reducing an interference component of the sensor signals comprises determining a presence of radiofrequency interference (RFI) in the environmental RF signals.

19. The method in accordance with claim 14, wherein reducing an interference component of the sensor signals comprises generating synthesized reference signals at least partially representative of the environmental RF signals and estimated interference parameters.

20. The method in accordance with claim 14, wherein generating reference signals from at least one reference coil comprises receiving environmental RF signals from a plurality of reference coils co-located with the active sensor coil.

* * * * *